US005965142A

United States Patent [19]

Dillon et al.

[11] Patent Number: 5,965,142

[45] Date of Patent: Oct. 12, 1999

[54] **POLYPEPTIDES AND METHODS FOR THE DETECTION OF *L. TROPICA* INFECTION**

[75] Inventors: Davin C. Dillon, Redmond; Steven G. Reed, Bellevue, both of Wash.

[73] Assignee: Corixa Corporation, Seattle, Wash.

[21] Appl. No.: 08/511,872

[22] Filed: Aug. 4, 1995

[51] Int. Cl.[6] ........................ A61K 38/00; A61K 39/002; C07K 2/00; C07K 14/00

[52] U.S. Cl. ..................................... 424/269.1; 424/184.1; 424/268.1; 530/300; 530/350

[58] Field of Search .............................. 424/184.1, 269.1, 424/268.1; 530/300, 350

[56] References Cited

U.S. PATENT DOCUMENTS 4,992,273 2/1991 Monjour et al. .

FOREIGN PATENT DOCUMENTS 0293827 7/1988 European Pat. Off. ..... G01N 35/569

8901045 9/1989 WIPO ............................. C12P 21/00

OTHER PUBLICATIONS

Campos–Nato et al, 1995, J. Exp. Med. 182: 1423–33.

Magill et al, 1992, JAMA, 267(11):1444–1446.

Jaffe et al, 1990. Clin. Exp. Immunol, 80:77–82.

Wilson et al, 1996, Gastroenteral Clin. of North Am., 25(3): 535–51.

Webb et al, 1996, J. Immunol., 157: 5034–5041.

Gardiner et al, 1983, Mol & Biochem Parasitol., 8:283–95.

Dillon et al, 1995, PNAS, 92: 7981–7985.

Howard et al, 1982, J of Immunol, 129(5):2206–2212.

Michiels et al, 1994, J. Oral Pathol. Med. 23:45–46.

Green et al, 1983, Trans. Roy. Soc. Trop. Med. & Hyg., 77(2):152–9.

Maul et al, 1982. Immunology of Parasitic Infection 2nd edition pp. 299–355.

Da Costa et al, 1996. Am. J. Trop. Med. Hyg., 55(5):511–515.

Webb et al, 1991. Mol. & Brochem. Parasitol, 48:173–184.

Yasir Skreiky et al., Antigens Shared by Leischmania Species and *Trypasnosoma cruzi:* Immunological Comparison of the Acidic Ribosomal P0 Proteins, *Infection and Immunity* 62:5, 1643–1651, 1994.

Manuel Soto et al., Isolation, characterization and analysis of the expression of the Leishmania ribosomal PO protein genes, *Molecular and Biochemical Parasitology* 61, 265–274, 1993.

Soto et al., Genomic Organization and Expression of Two Independent Gene Arrays Coding for Two Antigenic Acidic Ribosomal Proteins of Leishmania, *J. of Biological Chem.* 268:29, 21835–43,1993.

Yasir Skeiky et al., Cloning and Expression of *Trypanosoma cruzi* Ribosomal Protein P0 and Epitope Analysis of Anti–P0 Autoantibodies in Chagas' Disease Patients, *J. Exp. Med.* 176, 201–211, 1992.

James M. Burns, Jr. et al., Molecular characterization of a kinesin–related antigen of *Leishmania chagasi* that detects specific antibody in African and American visceral leishmaniasis, *Proc. Natl. Acad. Sci.* 90, 775–779, 1993.

Skeiky et al., A Recombinant Leishmania Antigen that Stimulates Human Peripheral Blood Mononuclear Cell to Express a Th1–Type Cytokine Profile and to Produce Interleukin 12, *Journal of Experimental Medicine* 181:4, 1527–1537, 1995.

Skeiky et al., Proliferative and Cytokine Responses of Human PBMC to Cloned *Leishmania Braziliensis* Heat Shock and Ribosomal Antigens, *Journal of Immunology* 150(8pt. 2):93A, Abstract #517, 1993.

Shapira et al., Sequence analysis and transcriptional activation of heat shock protein 83 of *Leischmania mexicana amazonensis, Molecular and Biochemical Parasitology* 42:2, 247–255, 1990.

Mongneau et al., Expression Cloning of a Protective Leishmania Antigen, Science 268, 563–566, 1995.

De Andrade et al., Recombinant Leishmania Hsp90 and Hsp70 are Recognized by Sera from Visceral Leishmaniasis Patient but not Chagas' Disease Patients, *J. of Clinical Microbiology* 30:2, 330–5, 1992.

*Primary Examiner*—Nita Minnifield
*Attorney, Agent, or Firm*—Seed and Berry LLP

[57] ABSTRACT

Compounds and methods for diagnosing *Leishmania tropica* infection, or for screening for *L. tropica* infection, are disclosed. The disclosed compounds are polypeptides that contain one or more epitopes of an *L. tropica* protein, Lt-210. The compounds are useful in a variety of in vitro and in vivo immunoassays for detecting *L. tropica* infection. The polypeptides are further useful in vaccines and pharmaceutical compositions for preventing leishmaniasis in individuals exposed to *L. tropica*.

13 Claims, 10 Drawing Sheets

```
CAGGCCCGCGTCCAGGCCCTCGAGGAGGCAGCGCGTCTCCGCGCGGAGCTGGAGGCGGCCGAGGAGGCGGCCCGCCTGGATGTCATGCAT    90
 Q  A  R  V  Q  A  L  E  E  A  A  R  L  R  A  E  L  E  A  A  E  E  A  A  R  L  D  V  M  H    30

GCGGCCGAGCAGGCCCGTGTCCAGGCCCTCGAGGAGGCAGCGCGTCTCCGCGCGGAGCTGGAGGAGGCCGAGGAGGCGGCCCGCCTGGAT   180
 A  A  E  Q  A  R  V  Q  A  L  E  E  A  A  R  L  R  A  E  L  E  E  A  E  E  A  A  R  L  D    60

GTCATGCATGCGGCCGAGCAGGCCCGCGTCCAGGCCCTCGAGGAGGCAGCGCGTCTCCGCGCGGAGCTGGAGGCTGCCGAGGAGGCGGCG   270
 V  M  H  A  A  E  Q  A  R  V  Q  A  L  E  E  A  A  R  L  R  A  E  L  E  A  A  E  E  A  A    90

CGCCTGGAGGCCATGCACGAGGCCGAGCAGGCCCGCTCCCAGGCCCTCGAGGAGGCAGCGCGTCTCCGCGCGGAGCTGGAGGAAGCCGAG   360
 R  L  E  A  M  H  E  A  E  Q  A  R  S  Q  A  L  E  E  A  A  R  L  R  A  E  L  E  E  A  E   120

GAGGCGGCCCGCCTGGATGTCATGCATGCGGCCGAGCAGGCCCGCGTCCAGGCCCTCGAGGAGGCAGCGCGTCTCCGCGCGGAGCTGGAG   450
 E  A  A  R  L  D  V  M  H  A  A  E  Q  A  R  V  Q  A  L  E  E  A  A  R  L  R  A  E  L  E   150

GAGGCCGAGGAGGCGGCCCGCCTGGAGGCCATGCACGAGGCCGAGCAGGCCCGCTCCCAGGCCCTCGAGGAGGCAGCGCGTCTCCGCGCG   540
 E  A  E  E  A  A  R  L  E  A  M  H  E  A  E  Q  A  R  S  Q  A  L  E  E  A  A  R  L  R  A   180

GAGCTGGAGGCGGCCGAGGAGGCGGCCCGCCTGGATGTCATGCACGAGGCCGAGCAGGCCCGTGTCCAGGCCCTCGAGGAGGCGGCGCGC   630
 E  L  E  A  A  E  E  A  A  R  L  D  V  M  H  E  A  E  Q  A  R  V  Q  A  L  E  E  A  A  R   210

CTGGATGTCATGCACGAGGCCGAGCAGGCCCGCGTCCAGGCCCTCGAGGAGGCAGCGCGTCTCCGCGCGGAGCTGGAGGCGGCCGAGGAG   720
 L  D  V  M  H  E  A  E  Q  A  R  V  Q  A  L  E  E  A  A  R  L  R  A  E  L  E  A  A  E  E   240

GCGGCCCGCCTGGATGTCATGCACGAGGCCGAGCAGGCCCGCGTCCAGGCCCTCGAGGAGGCAGCGCGTCTCCGCGCGGAGCTGGAGGCG   810
 A  A  R  L  D  V  M  H  E  A  E  Q  A  R  V  Q  A  L  E  E  A  A  R  L  R  A  E  L  E  A   270

GCCGAGGAGGCGGCCCGCCTGGATGTCATGCACGAGGGCGAGCAGGCCCGTGTCCAGGCCCTCGAGGAGGCGGCCCGCCTGGAGGCCATG   900
 A  E  E  A  A  R  L  D  V  M  H  E  G  E  Q  A  R  V  Q  A  L  E  E  A  A  R  L  E  A  M   300

CACGAGGCCGAGCAGGCCCGCTCCCAGGCCCTCGAGGAGGCAGCGCGTCTCTGCGCGGAGCTGGAGGCTGAGGAGGAGGAAAAAGATGAG   990
 H  E  A  E  Q  A  R  S  Q  A  L  E  E  A  A  R  L  C  A  E  L  E  A  E  E  E  E  K  D  E   330

CGGCCGGCGACGTCGAGCTACAGCGAGGAGTGCAAAGGGCGACTGCTATCGAGGGCGCGGCCGGATCCGCGGAGGCCGCTGCCGCGGCCG  1080
 R  P  A  T  S  S  Y  S  E  E  C  K  G  R  L  L  S  R  A  R  P  D  P  R  R  P  L  P  R  P   360

TTCATTGGGATGTCACTGTTGGAGGATGTGGAGAAGAGTATTCTCATTGTGGACGGGCTCTACAGGGATGGGCCGGCGTACCAGACGGGC  1170
 F  I  G  M  S  L  L  E  D  V  E  K  S  I  L  I  V  D  G  L  Y  R  D  G  P  A  Y  Q  T  G   390

ATCCGCCTCGGGGATGTCCTCTTGCGTATCGCGGGGGTTTACGTGGATTCAATAGCGAAGGCGAGGCAGGTGGTCGATGCGCGTTGCCGC  1260
 I  R  L  G  D  V  L  L  R  I  A  G  V  Y  V  D  S  I  A  K  A  R  Q  V  V  D  A  R  C  R   420

TGCGGCTGCGTCGTTCCCGTGACGCTGGCGACGAAGATGAACCAGCAGTACAGCGTGGCTCTGTATATCATGACGGTGGATCCGCAGCAC  1350
 C  G  C  V  V  P  V  T  L  A  T  K  M  N  Q  Q  Y  S  V  A  L  Y  I  M  T  V  D  P  Q  H   450

AACGACAAGCCCTTTTTTTTTGATGTGCACATCCACCACCGCATCGAGAGCTCGCACATGGGGAAGAAGGCGCAGTGGATGGAAGTTCTT  1440
 N  D  K  P  F  F  F  D  V  H  I  H  H  R  I  E  S  S  H  M  G  K  K  A  Q  W  M  E  V  L   480

GAGAGCCCATCCGTATCTTCGGCTGCCACCACCCCTCTCGTGCCGCTCTTGCGTGAGCCGACGCCGCGTAGGGGCTCAGAGCTGCAGTCA  1530
 E  S  P  S  V  S  S  A  A  T  T  P  L  V  P  L  L  R  E  P  T  P  R  R  G  S  E  L  Q  S   510

AGTGCTCGTTCCGCCTTCGTTGCCACGTCTTACTTCTCGAGCGCGCGCAGGTCGGTCAGCTCAGAAAGTGAGCGACCGCGCGGGTCCTCT  1620
 S  A  R  S  A  F  V  A  T  S  Y  F  S  S  A  R  R  S  V  S  S  E  S  E  R  P  R  G  S  S   540

AGCGTGGCTATGGCGGAGGAGGCGATCGCGCTGGCGCCGCAAGGGTATACCCCACCCAACCAAGTGCGCGGCCGTAGTTGACGTCTCTGT  1710
 S  V  A  M  A  E  E  A  I  A  L  A  P  Q  G  Y  T  P  P  N  Q  V  R  G  R  S  *            566

GTGAGTGTGTGTCGCTCCGTCTCCTTCCTTTTTCGTCATGTGTTTATTCATTTCTTTTTC                                1771
```

```
      V                   R         A A                 D V     A A
Q A R   Q A L E E A A R L   A E L E     E E A A R L         M H     E
      S                   C         E E                 E A     E G
```

QARVQALEEAARLRAELEAAEEAARLDVMHAAE

*Fig. 1C*

QARVQALEEAARLRAELEEAEEAARLDVMHAAE

*Fig. 1D*

QARVQALEEAARLRAELEAAEEAARLEAMHEAE

*Fig. 1E*

QARSQALEEAARLRAELEEAEEAARLDVMHAAE

*Fig. 1F*

QARVQALEEAARLRAELEEAEEAARLEAMHEAE

*Fig. 1G*

QARSQALEEAARLRAELEAAEEAARLDVMHEAE

*Fig. 1H*

QARVQALEEAARLRAELEAAEEAARLDVMHEAE

*Fig. 1I*

QARVQALEEAARLRAELEAAEEAARLDVMHEGE

*Fig. 1J*

POLYPEPTIDES AND METHODS FOR THE DETECTION OF *L. TROPICA* INFECTION

STATEMENT OF GOVERNMENT INTEREST

The U.S. Government has an interest in this application pursuant to Grant No. DAMD17-96-1-6065 awarded by the U.S. Department of the Army.

TECHNICAL FIELD

The present invention relates generally to diagnosis of Leishmania infection, and more specifically, to the use of Leishmania polypeptides in diagnosis methods and as vaccines for immunizing an individual against leishmaniasis.

BACKGROUND OF THE INVENTION

Leishmania organisms are intracellular protozoan parasites of macrophages that cause a wide range of clinical diseases in humans and other animals. The pathological outcomes range from simple self-healing cutaneous lesions in cutaneous leishmaniasis (CL) to acute visceral leishmaniasis, commonly referred to as kala-azar. Symptoms of visceral disease include fever, emaciation, hyper gammaglobulinanemia, hepatosplenomegaly, and pancytopenia. Although *L. tropica* generally causes cutaneous leishmaniasis, a variant form of visceral disease caused by *L. tropica* has been noted. Exposure of a yet unknown number of individuals during the Gulf War to *L. tropica* has resulted in a variant form of visceral disease, referred to as viscerotropic leishmaniasis (VTL). Symptoms associated with VTL differ somewhat from classical visceral disease in that some patients lack both fever and hepatosplenomegaly but have chronic weakness and malaise. More importantly, serum antibody titers to Leishmania are significantly lower than those observed in patients with classical visceral leishmaniasis (VL).

The latency period observed with leishmanial infection can be extensive, with asymptomatic periods of greater than ten years not uncommon. Occasionally, parasitic infection is detected only when the individual has entered an immunocompromised state. This extended latency period increases the risk of further transmission of the parasite. There are documented cases of transfusion-acquired leishmaniasis, even from asymptomatic individuals. In addition, experiments have demonstrated the survival of *L. tropica* parasites in blood products during storage for up to a month.

Early diagnosis of leishmaniasis is critical for successful treatment but is difficult to achieve with existing techniques. The recent experience of leishmaniasis associated with Desert Storm has underlined a fundamental problem in the diagnosis of one of the world's most widespread protozoal infections; there are no simple, effective, and reliable diagnostic tests. Diagnosis of classical VL has exploited the elevated antibody response to parasite antigens in tests involving serological reactivity to whole or lysed promastigotes or to recombinant antigens. Confirmation of infection is generally made by the isolation of live parasites from spleen, liver, bone marrow, or lymph nodes. However, these tests are not without disadvantages. Tests relying on the use of whole parasites or crude lysates are difficult to standardize. In addition, preparation of the test antigens is expensive and difficult on a large scale.

Diagnosis of leishmaniasis in VTL patients is generally unsuccessful using current test strategies. In particular, the serological test antigens are generally disrupted promastigotes, and in VTL patients, antibody reactivity to these antigens is low. Thus, currently available methods often fail to detect this potentially fatal disease early enough to allow effective treatment.

In addition, currently there are no vaccines against Leishmania, in spite of the public health importance of this disease. Protective immunity against Leishmania is mediated by T cells, and Th1 cells in particular. An antigen capable of stimulation of such protective T cells would be a vaccine candidate.

Accordingly, there is a need in the art for more sensitive and specific methods for detecting and protecting against Leishmania infections resulting in VTL. The present invention relies on immunodominant antigens of Leishmania that allow detection of both humoral and cellular immune responses, while providing other related advantages.

SUMMARY OF THE INVENTION

Briefly stated, the present invention provides polypeptides and methods for determining the presence of and protecting against Leishmania infection in patients and in blood supplies, and for evaluating the capability of a patient for generating an immune response to Leishmania. In one aspect, the present invention provides Lt-210 polypeptides or a portion thereof. In a related aspect, the polypeptide comprises at least one repeat sequence of Lt-210. In yet another related aspect, the polypeptide is selected from the group consisting of FIG. 1C (SEQ ID NO: 4), FIG. 1D (SEQ ID NO: 5), FIG. 1E (SEQ ID NO: 6), FIG. 1F (SEQ ID NO: 7), FIG. 1G (SEQ ID NO: 8), FIG. 1H (SEQ ID NO: 9), FIG. 11 (SEQ ID NO: 10), and FIG. 1J (SEQ ID NO: 11). In one embodiment, the polypeptide comprises the amino acid sequence Gln-Ala-Arg-Xaa-Gln-Ala-Leu-Glu-Glu-Ala-Ala-Arg-Leu-Xbb-Ala-Glu-Leu-Glu-Xcc-Xcc-Glu-Glu-Ala-Ala-Arg-Leu-Xdd-Xee-Met-His-Xcc-Xff-Glu (SEQ ID NO:3), wherein Xaa is Val or Ser; Xbb is Arg or Cys; Xcc is Ala or Glu; Xdd is Asp or Glu; Xee is Val or Ala; and Xff is Ala or Gly. In yet another related aspect, the polypeptide comprises an epitope bound by an antibody to Lt-210. In other aspects, the polypeptide has an amino acid sequence as shown in FIG. 1A (SEQ ID NO: 2).

In still other aspects, DNA molecules encoding Lt-210 or a portion thereof are provided. In a related aspect, the DNA molecule has the nucleotide sequence shown in FIG. 1A (SEQ ID NO: 1). In yet another related aspect, the DNA molecule encodes any of the polypeptides provided herein. Recombinant expression vectors containing a DNA molecule as described herein are provided. In certain embodiments, a host cell is transformed with the expression vector. Suitable host cells include bacteria, yeast, insect cell lines, and mammalian cell lines.

In another aspect of this invention, methods for determining the presence of Leishmania infection in a patient are disclosed, comprising: (a) contacting a biological sample from a patient with a polypeptide as provided herein; and (b) detecting in the biological sample the presence of antibodies that bind to the polypeptide, and therefrom determining the presence of Leishmania infection.

In another aspect of the present invention, methods for determining the presence of Leishmania infection in a patient are provided, comprising: (a) injecting intradermally a polypeptide as provided herein; and (b) detecting a delayed-type hypersensitivity reaction to the polypeptide, and therefrom determining the presence of Leishmania infection.

In yet another aspect of this invention, methods for evaluating a patient's capability for generating an immune response to Leishmania are provided, comprising: (a) contacting a biological sample obtained from a patient with a polypeptide as discussed above, wherein the biological sample comprises peripheral blood mononuclear cells, monocytes, B cells, dendritic cells, macrophages or combinations thereof, and (b) measuring an activity of the cells, and thereby determining whether a patient can generate an immune response. In certain embodiments, the activity of the cells is a proliferative response. In yet other embodiments, the activity is secretion of a cytokine or expression of mRNA encoding a cytokine.

Within related aspects, the present invention provides diagnostic kits for identifying a patient infected with *Leishmania tropica*, comprising a polypeptide as provided herein, and a detection reagent.

In yet other aspects, vaccines for stimulating a protective immune response, comprising a polypeptide as discussed herein in combination with a suitable carrier or diluent are provided. Within related aspects, pharmaceutical compositions, comprising the above polypeptides and a physiologically acceptable carrier are also provided.

These and other aspects of the present invention will become apparent upon reference to the following detailed description and attached drawings. In addition, various references are set forth below which describe in more detail certain procedures or compositions. Each of these references are incorporated herein by reference in their entirety as if each were individually noted for incorporation.

BRIEF DESCRIPTION OF THE DRAWINGS

FIG. 1 is a DNA sequence (SEQ ID NO: 1) of a representative clone Lt-1, which expresses a portion of Lt-210 and the predicted amino acid sequence (SEQ ID NO: 2) of the open reading frame. The 33 amino acid repeats in the sequence are underlined (A). The 33 amino acid repeat is shown with the alternate amino acids found in the native protein (B). The repeat sequences found in the Lt-1 clone are shown in (C)–(J) (SEQ ID NOS: 4–11).

DETAILED DESCRIPTION OF THE INVENTION

Figures 2A, 2B:
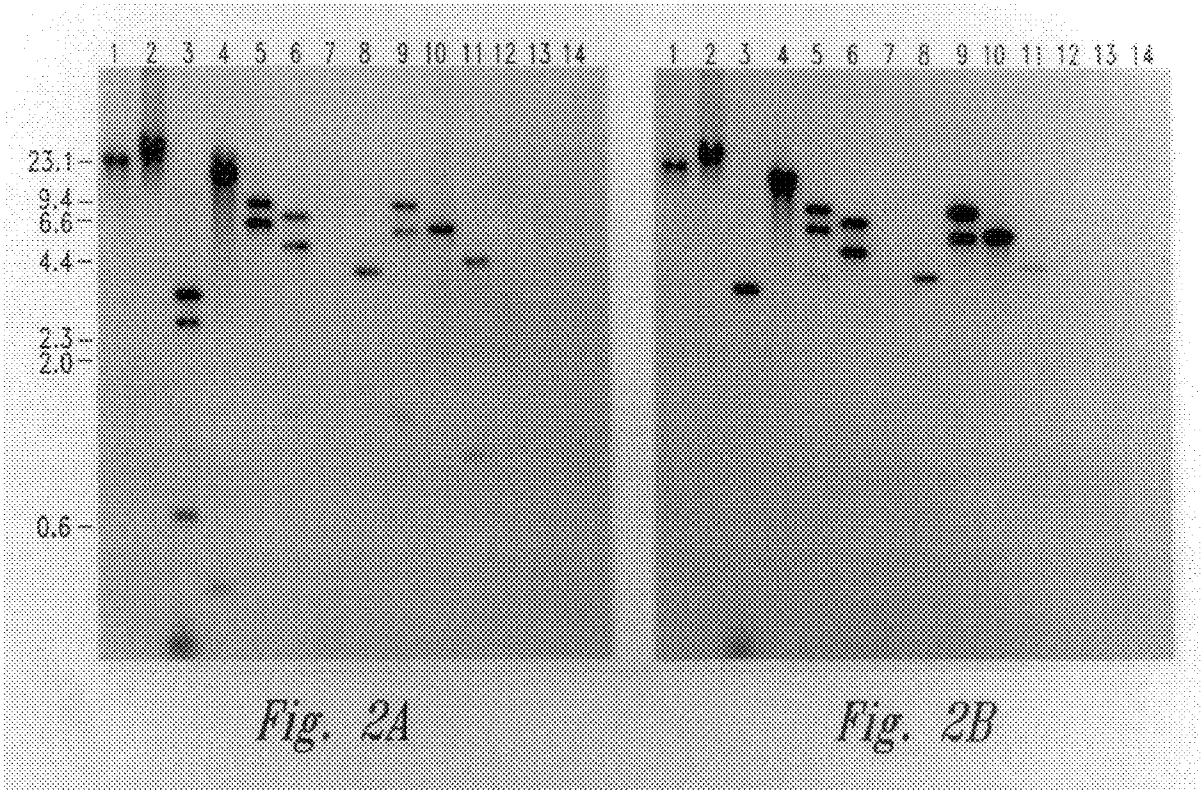
FIG. 2 is a Southern blot analysis probed with sequences of Lt-1 and Lt-2, a second representative clone, which expresses a portion of Lt-210. Genomic DNA of *L. tropica* was digested with EcoRI (lane 1), Xba I (lane 2), Xho I (lane 3), BamH I (lane 4), Hind III (lane 5), and Pst I (lane 6). *L. major* (lane 7), *L. donovani* (lane 8), *L infantum* (lane 9), *L. chagasi* (lane 10), *L. amazonensis* (lane 11), *L. braziliensis* (lane 12), *L. guyanensis* (lane 13), and *T. cruzi* (lane 14) were digested with Pst I. Blots were probed with the Lt-1 sequence (A) or the Lt-2 sequence (B).

As noted above, the present invention is generally directed to polypeptides and methods useful for detecting and protecting against Leishmania infection in patients and in blood supplies. The polypeptides generally comprise one or more antigenic epitopes of an *L. tropica* protein. In particular, polypeptides comprising at least one repeat sequence of Lt-210, a *Leishmania tropica* protein, are provided. The use of such polypeptides for detecting infected patients, for preventing infection and for evaluating a patient's capability to generate an immune response to Leishmania are also provided.

As used herein, "Lt-210" refers to an immunogenic protein molecule of approximately 210 kD expressed by *L. tropica* that binds to antibodies found in *L. tropica*-infected patients. Lt-210 contains repeat amino acid sequences as defined above, as well as non-repeat amino acid sequences. A "portion" of Lt-210 is at least 20 amino acids which has one or more of the immunogenic properties as described below. The 20 amino acids may be derived from either repeat sequence or from non-repeat sequence. An "epitope" bound by an antibody to Lt-210 comprises at least a single repeat unit, and may contain additional sequences at the N- or C-terminus that are derived from native Lt-210 sequences or from another protein.

For purposes of the present invention, "repeat sequence" refers to a 33 amino acid sequence found repeated in the Lt-210 protein of *L. tropica*. These sequences are imprecisely repeated (i.e., not every sequence is identical). Besides the known variants depicted in FIG. 1B through FIG. 1J, in the context of the present invention, other variants of the repeat sequence include conservative substitutions or modifications, such that they retain the immunogenic properties of the recited polypeptide, described in more detail below.

In particular, such variants may generally be identified by modifying the polypeptide sequence as described below and evaluating the immunogenic properties of the modified polypeptide using, for example, one or more of the assays described herein. A "conservative substitution" in the context of the subject invention is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Preferred substitutions include changes between val and ser, arg and cys, ala and glu, asp and glu, val and ala, and ala and gly. Variants may also, or alternatively, contain other modifications, including the deletion or addition of amino acids that have minimal influence on the antigenic properties, secondary structure and hydropathic nature of the polypeptide. For example, the polypeptide may be conjugated to a linker or other sequence for ease of synthesis or to enhance binding of the polypeptide to a solid support.

"Non-repeat" sequence refers to amino acid sequences of Lt-210 that do not contain more than 50% sequence identity with the 33 amino acid repeat, or are derived therefrom. The amino acid sequence from residues 327 to 566 in FIG. 1 is an example of a non-repeat sequence. The non-repeat sequences used as described herein may contain conservative substitutions, or other modifications (e.g., additions, deletions) as described above.

In one aspect of the invention, DNA molecules encoding Lt-210 or a portion thereof, such as one or more repeat sequences, are provided. DNA encoding the Lt-210 protein may be isolated from genomic DNA or cDNA by any one of a number of standard methods. For instance, nucleotide sequences encoding Lt-210 may be isolated by expression screening of a genomic *L. tropica* library using sera from *L. tropica*-infected patients. Within the examples described herein, genomic DNA from an infected VTL patient was isolated and sheared to fragments in a size range of 2–6 kilobases. Adapters containing EcoRI sites were added and the inserts were cloned into lambda Zap II (Stratagene, La Jolla, Calif.). A pool of patient sera pre-absorbed on *E. coli* lysate was used to detect clones expressing at least a portion of Lt-210. The DNA sequence of one preferred clone, Lt-1, expresses a portion of Lt-210 and contains both repeat sequences and non-repeat sequences and is described in more detail herein (FIG. 1). Alternatively, a clone encoding Lt-210 may be isolated from a cDNA or genomic library by hybridization to an oligonucleotide probe derived from the sequence of Lt-1 provided herein. A genomic library may be prepared as described above and in the examples, or by restriction digestion of genomic DNA with an enzyme leaving compatible cloning ends, and inserted into an appropriate vector, such as λZAP Express, λgt10, pWE15, λZAPII, λEMBL3 or λEMBL4. A cDNA library may be prepared by reverse transcriptase synthesis of mRNA isolated from *L. tropica* using an oligo dT primer, random primer, or a sequence specific primer that is complementary to the sequence of Lt-1 provided herein. Specific 5' and 3' ends of the gene may be obtained by the RACE method (Frohman et al., *Proc. Natl. Acad. Sci. USA* 85:8998–9002, 1988), ligation-anchored PCR (Troutt et al., *Proc. Natl. Acad. Sci. USA* 89:9823–9825, 1992) or other similar methods. Verification that a clone contains Lt-210 sequence may be obtained by determining the DNA sequence of the clone insert and comparing it to the sequence of Lt-1 provided herein. Sequence identity of 90% or better over the region of overlap between the clones indicates that the clone encodes Lt-210 or a portion thereof. Overlap may be identified by restriction endonuclease mapping, by computer programs designed to align multiple sequences, or the like. Some mismatch may be due to variations among strains of *L. tropica* or DNA sequence errors. Alternatively, the DNA molecules may be expressed and tested for reactivity with antibodies to the Lt-210 molecule, such as monoclonal antibodies as described herein.

The detection of clones described above may be generally performed using methods known to those of ordinary skill in the art, such as methods described in Sambrook et al., *Molecular Cloning: A Laboratory Manual*, Cold Spring Harbor Laboratories, Cold Spring Harbor, N.Y., 1989, which is incorporated herein by reference. Briefly, for antibody screening, a bacteriophage or plasmid expression library is plated and transferred to filters. The filters are then incubated with serum and a detection reagent. In the context of the present invention, a "detection reagent" is any compound capable of binding to the antibody-antigen complex, which may then be detected by any of a variety of means known to those of ordinary skill in the art. Preferred detection reagents contain a "binding agent," such as Protein A, Protein G, IgG, avidin or a lectin, coupled to a reporter group. Suitable reporter groups include, but are not limited to, enzymes, substrates, cofactors, inhibitors, dyes, radioisotopes, luminescent molecules, fluorescent molecules and biotin. Preferably, the reporter group is horseradish peroxidase, which may be detected by incubation with a substrate such as tetramethylbenzidine or 2,2'-azino-di-3-ethylbenzthiazoline sulfonic acid. Plaques or colonies containing genomic DNA or cDNA sequences that express a protein which binds to an antibody in the serum may be isolated and purified by techniques known to those of ordinary skill in the art. Appropriate methods may be found, for example, in Sambrook et al., supra.

Identification of clones containing Lt-210 DNA may also be made by probe hybridization to either a bacteriophage or plasmid library. Preferably, the library is constructed in a bacteriophage vector. Merely by way of example, screening is described for a phage library. Lambda phage containing *L. tropica* inserts are absorbed onto *E. coli*, such as LE392 or C600, and plated. After incubation overnight, plates are chilled and phages are transferred onto nitrocellulose or nylon filters. The filters are treated with base, neutralized, and DNA is fixed to the filters either by baking in vacuo or UV-irradiation. The filters are then prehybridized with buffer containing bovine serum albumin, 5×SSPE, and 5× Denhardt's. The probe may be a fragment isolated from a clone containing a portion of the Lt-210 gene or a synthetically prepared oligonucleotide based on sequence presented herein. The probe is labeled by a standard technique, such as nick translation or end-labeling (see Sambrook et al., supra). Radiolabeled probe is hybridized overnight in 5×SSPE, 1× Denhardt's, 0.5% SDS and optionally 50% formamide at a predetermined temperature based on the probe length, salt, and formamide concentration. Following hybridization, filters are washed at conditions equivalent to hybridization conditions. Plaques containing sequences complementary to the probe are visualized by autoradiography or phosphor image analysis. Positive plaques are purified and the inserts isolated.

As noted above, the present invention also provides repeat sequence polypeptides of the Lt-210 protein. Repeat sequences of Lt-210 generally are identified by a sequence analysis of the protein. In FIG. 1, A through J, multiple 33 base pair repeats are shown. Such repeat sequences are variants as described herein; at certain positions, alternate amino acid residues are found in the native protein (see FIG. 1B). Repeat sequences comprising any of these variants may be used in the present invention. In addition, as discussed above, other variants containing conservative amino acid substitutions may also be used in this invention. Conservative amino acid substitutions may be made at the known variant positions or at any other position, as long as the repeat sequences retain one or more immunogenic properties as set forth in one of the assays described in more detail below. Such assays include ELISA using sera or antibodies from Leishmania-infected patients or antibodies raised in experimental animals, delayed-type hypersensitivity, induction of cytokine expression (e.g., γ-interferon), and induction of proliferation in vitro (described in more detail below). For a repeat sequence an ELISA is a preferred assay. As described herein, a portion of Lt-210 containing at least a 33 amino acid repeat as shown in FIGS. 1A through 1J generates a sufficient signal in an ELISA, thereby indicative of infection. Accordingly, a polypeptide comprising at least the 33 amino acids of the repeat sequence of Lt-210 contains an epitope that is bound by an antibody to Lt-210. Such polypeptides (and variants thereof) may be used in this invention. In preferred embodiments, two or three tandemly arranged repeat sequences are used. These multiple repeat sequences are joined through a peptide linkage to form a single amino acid chain. They may be joined directly or by way of a linker sequence (e.g., gly-gly) that does not significantly alter the immunogenic properties of the repeat sequences and corresponding epitopes. One such multiple repeat sequence, Lt-1r, contains 1 and ⅓ repeat sequences. Repeat sequence may also be used in the present invention in combination (e.g., linked) with non-repeat sequence.

In addition, a portion of the Lt-210 molecule used in this invention may comprise a non-repeated sequence. Such sequence may be identified as encoding or containing an amino acid sequence other than a 33 amino acid repeat or derivative of a repeat sequence as depicted in FIGS. 1A and 1B. The amino acid sequence from residues 327 to 566 in FIG. 1 is an example of a non-repeated sequence. Such sequences may be isolated by PCR using primers corresponding to sequence information provided herein or by isolation of a clone hybridizing to probes containing non-repeated sequences. Clones may be screened and isolated as described above. Suitability of a non-repeat sequence for use in this invention may be determined by the immunological assays described below. These assays include ELISA using sera or antibodies from patients or antibodies raised in experimental animals, delayed-type hypersensitivity, induction of cytokine expression and induction of proliferation in vitro (described in more detail below). A non-repeat sequence may be used alone or in combination with one or more repeat sequences.

Immunogenic properties of polypeptides described herein, including repeat and non-repeat sequences, and variants thereof, may be determined by one or more of the following immunological assays: ELISA, delayed-type hypersensitivity, induction of cytokine expression, and induction of proliferation in vitro. Within each of these assays, the suitability of a polypeptide is established by comparison to a reference standard, which is the entire Lt-1 polypeptide from amino acid residues 1 to 566 (see FIG. 1).

Briefly, in an ELISA, the polypeptide or the reference standard is adsorbed to the well of a test plate. Control sera or antibodies and sera from a patient known to be infected with Leishmania or a monoclonal or polyclonal antibody, prepared as described below, are added to the wells. Unbound antibody is washed out and a detection reagent added. The polypeptide is suitable for use herein if it generates a signal with a positive sera that is at least three standard deviations above the predetermined cut-off value established as the average mean signal obtained from uninfected patient samples or from a Receiver Operator Curve cutoff (Sackett et al, infra), and differentiates positives and negatives equivalent to or better than the reference standard.

Similarly, when the immunogenic property is eliciting a DTH reaction, the polypeptide is compared to the reference standard. For this comparison, it is convenient to elicit DTH in an experimental animal, typically a mouse or rat. Briefly, the polypeptide and reference standard are injected intradermally in the ear or foot pads of an infected animal. Swelling is measured at approximately 24–48 hours. The polypeptide is suitable if it elicits swelling of 0.1 to 5 mm, which may be corroborated by histological evidence of mononuclear cell infiltration. In humans, swelling should be at least 5 mm diameter.

Protein and mRNA cytokine expression or cell proliferation may be assayed in vitro. Briefly, cells from an infected experimental animal or human are cultured with polypeptide or reference standard for five days. Proliferation or cytokine expression is then measured. Proliferation is then measured following pulse labeling with $^3$H-thymidine. The polypeptide is suitable if the stimulation index is greater than or equal to 5. Cytokine expression of RNA may be measured by PCR, Northern blotting or RNase probe protection. IFN-γ is a preferred cytokine to measure in this assay. Briefly, IFN-γ protein is measured by a capture ELISA, as described below. For either mRNA or protein production, the polypeptide should achieve levels above baseline, preferably at least two-fold.

The polypeptides of the subject invention may be generated using techniques well known to those of ordinary skill in the art. Polypeptides having fewer than about 100 amino acids, and generally fewer than about 50 amino acids, can be synthesized using, for example, the Merrifield solid-phase synthesis method, where amino acids are sequentially added to a growing amino acid chain. (See Merrifield, *J. Am. Chem. Soc.* 85:2149–2146, 1963.) Equipment for automated synthesis of polypeptides is commercially available from suppliers such as Applied Biosystems, Inc. (Foster City, Calif.) The Lt-210 sequence or portions thereof, including repeat sequences, may be synthesized by this method.

Alternatively, the polypeptides described herein may be prepared by expression of recombinant DNA encoding the polypeptide in cultured host cells. Preferably, the host cells are bacteria, such as *E. coli*, yeast, an insect cell line, such as Spodoptera or Trichoplusia, or a mammalian cell line, including (but not limited to) CHO, COS and NS-1. The DNA sequences expressed in this manner may encode Lt-210, a portion of Lt-210, including repeat sequences, non-repeat sequence, a variant of such proteins, or the like. Expressed polypeptides of this invention are generally isolated in substantially pure form. Preferably, the polypeptides are isolated to a purity of at least 80% by weight, more preferably, to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography.

DNA sequences encoding the polypeptides provided by this invention can be assembled from DNA fragments and short oligonucleotide linkers, or from a series of oligonucleotides, to provide a synthetic gene which is capable of being inserted in a recombinant expression vector.

Recombinant expression vectors contain a DNA sequence encoding any of the polypeptides described herein, operably linked to suitable transcriptional or translational regulatory elements derived from mammalian, microbial, viral or insect genes. A necessary regulatory element is a transcriptional promoter. Optional regulatory elements include an operator sequence to control transcription, a sequence encoding suitable ribosomal binding sites, and sequences which control the termination of transcription and translation. An origin of replication and a selectable marker to facilitate identification of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; and a ribosome binding site is operably linked to a coding sequence if it is positioned so as to permit translation. Generally, operably linked means contiguous and, in the case of secretory leaders, in reading frame. DNA sequences encoding polypeptides as described herein which are to be expressed in a microorganism will preferably contain no introns that could prematurely terminate transcription.

Expression vectors for bacterial use may include a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden), pGEM1 (Promega Biotec, Madison, Wis., U.S.A.), pET 11a, pET 15b (Novagen, Madison, Wis.), and the like.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), T7 promoter, β-galactosidase promoter, tryptophan (trp) promoter system (Goeddel et al., *Nucl. Acids Res.* 8:4057, 1980; and European Patent Application 36,776) and the tac promoter (Maniatis, *Molecular Cloning: A Laboratory Manual*, Cold Spring Harbor Laboratory, p. 412, 1982). A particularly useful bacterial expression system employs the $P_L$ promoter and cI857ts thermolabile repressor or β-gal promoter and $lacI^q$ repressor. Plasmid vectors available from the American Type Culture Collection which incorporate derivatives of the $\lambda P_L$ promoter include plasmid pHUB2, resident in *E. coli* strain JMB9 (ATCC 37092) and pPLc28, resident in *E. coli* RR1 (ATCC 53082). Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., European Patent Application 73,657.

Preferred yeast vectors can be assembled using DNA sequences from pBR322 for selection and replication in *E. coli* ($Amp^r$ gene and origin of replication) and yeast DNA sequences, such as a glucose-repressible ADH2 (Russell et al., *J. Biol. Chem.* 258:2674, 1982; Beier et al., *Nature* 300:724, 1982) promoter and α-factor secretion leader, which can be inserted between the promoter and the structural gene to be expressed. (See, e.g., Kurjan et al., *Cell* 30:933, 1982; Bitter et al., *Proc. Natl. Acad. Sci. USA* 81:5330, 1984.) The leader sequence may be modified to contain near its 3' end one or more useful restriction sites to facilitate fusion of the leader sequence to foreign genes.

The transcriptional and translational control sequences in expression vectors to be used in transforming vertebrate cells may be provided by viral sources. For example, commonly used promoters and enhancers are derived from polyoma, adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978) or a 250 bp Hind III/Bgl II fragment. Exemplary vectors can be constructed as disclosed by Okayama and Berg, *Mol. Cell. Biol.* 3:280, 1983.

A preferred eukaryotic vector for expression of Lt-210 protein DNA is pDC406 (McMahan et al., *EMBO J.* 10:2821, 1991), and includes regulatory sequences derived from SV40, human immunodeficiency virus (HIV), and Epstein-Barr virus (EBV). Other preferred vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been deleted, making the Bgl II site within the multiple cloning site unique.

A useful cell line that allows for episomal replication of expression vectors, such as pDC406 and pDC409, which contain the EBV origin of replication, is CV-1/EBNA (ATCC CRL 10478). The CV-1/EBNA cell line was derived by transfection of the CV-1 cell line with a gene encoding Epstein-Barr virus nuclear antigen-1 (EBNA-1) and constitutively expresses EBNA-1 from the human CMV immediate-early enhancer/promoter.

Transformed host cells are cells which have been transformed or transfected with expression vectors constructed using recombinant DNA techniques and which contain sequences encoding an Lt-210 polypeptide of the present invention. Transformed host cells may express the desired Lt-210 polypeptide, but host cells transformed for purposes of cloning or amplifying Lt-210 DNA do not need to express the Lt-210 protein. Expressed Lt-210 proteins will preferably be secreted into the culture supernatant.

Suitable host cells for expression of recombinant proteins include prokaryotes, such as *E. coli*, yeast, or higher eukaryotic cells under the control of appropriate promoters. Higher eukaryotic cells include established cell lines of insect or mammalian origin as described below. Cell-free translation systems could also be employed to produce Lt-210 proteins using RNAs derived from the DNA constructs disclosed herein. Appropriate cloning and expression vectors for use with bacterial, fungal, yeast, and mammalian cellular hosts are described, for example, by Pouwels et al. (*Cloning Vectors. A Laboratory Manual*, Elsevier, N.Y., 1985).

Prokaryotic expression hosts may be used for expression of polypeptides. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphylococcus, although other hosts may also be employed.

Recombinant polypeptides as described herein may also be expressed in yeast hosts, preferably from the Saccharomyces species, such as *S. cerevisiae*. Yeast of other genera, such as Pichia or Kluyveromyces may also be employed. Yeast vectors will generally contain an origin of replication from the 2$\mu$ yeast plasmid or an autonomously replicating sequence (ARS), a promoter, DNA encoding the Lt-210 polypeptide, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and the *S. cerevisiae* trp1 gene, which provides a selection marker for a mutant strain of yeast lacking the ability to grow in tryptophan. Yeast vectors contain a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable yeast transformation protocols are known to those of skill in the art. An exemplary technique described by Hind et al. (*Proc. Natl. Acad. Sci. USA* 75:1929, 1978) involves selecting for $Trp^+$ transformants in a selective medium consisting of 0.67% yeast nitrogen base, 0.5% casamino acids, 2% glucose, 10 mg/ml adenine and 20 mg/ml uracil. Host strains transformed by vectors comprising the ADH2 promoter may be grown for expression in a rich medium consisting of 1% yeast extract, 2% peptone, and 1% glucose supplemented with 80 mg/ml adenine and 80 mg/ml uracil. Derepression of the ADH2 promoter occurs upon exhaustion of medium glucose. Crude yeast supernatants are harvested by filtration and held at 4° C. prior to further purification.

Various mammalian or insect (e.g., Spodoptera or Trichoplusia) cell culture systems can also be employed to express recombinant protein. Baculovirus systems for production of heterologous proteins in insect cells are reviewed, for example, by Luckow and Summers, *Bio/Technology* 6:47, 1988. Examples of suitable mammalian host cell lines include the COS-7 lines of monkey kidney cells, described by Gluzman, *Cell* 23:175, 1981, and other cell lines capable of expressing an appropriate vector including, for example, CV-1/EBNA (ATCC CRL 10478), L cells, C127, 3T3, Chinese hamster ovary (CHO), COS, NS-1, HeLa and BHK cell lines. Mammalian expression vectors comprise nontranscribed elements such as a suitable promoter and optional enhancer linked to the gene to be expressed, and may comprise other 5' or 3' flanking nontranscribed or nontranslated sequences, such as ribosome binding sites, a polyadenylation site, splice donor and acceptor sites, and transcriptional termination sequences.

Purified polypeptides may be prepared by culturing suitable host/vector systems to express the recombinant translation products of the DNAs of the present invention, which are then purified from culture media or cell extracts. For example, supernatants from systems which secrete recombinant protein into culture media may be first concentrated using a commercially available protein concentration filter, such as an Amicon or Millipore Pellicon ultrafiltration unit. Following the concentration step, the concentrate may be applied to a suitable purification matrix. For example, a suitable affinity matrix may comprise a counter structure protein (i.e., a protein to which a polypeptide binds in a specific interaction based on structure) or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying polypeptides.

Affinity chromatography is a particularly preferred method of purifying polypeptides. By way of example, an Lt-210 polypeptide expressed as a fusion protein comprising an immunoglobulin Fc region can be purified using Protein A or Protein G affinity chromatography. Moreover, an Lt-210 polypeptide linked to a HisTag sequence may be purified by metal chelation chromatography. Monoclonal antibodies against a Lt-210 polypeptide may also be useful in affinity chromatography purification.

Finally, one or more reverse-phase high performance liquid chromatography (RP-HPLC) steps employing hydrophobic RP-HPLC media (e.g., silica gel having pendant methyl or other aliphatic groups) can be employed to further purify protein composition. Some or all of the foregoing purification steps, in various combinations, can also be employed to provide a homogeneous recombinant protein.

Recombinant polypeptides produced in bacterial culture are preferably isolated by initial extraction from disrupted cell pellets, followed by one or more concentration, salting-out, aqueous ion exchange or size exclusion chromatography steps. High performance liquid chromatography (HPLC) may be employed for final purification steps.

Fermentation of yeast which express Lt-210 polypeptides as a secreted protein greatly simplifies purification. Secreted recombinant protein resulting from a large-scale fermentation can be purified by methods analogous to those disclosed by Urdal et al., *J. Chromatog* 296:171, 1984.

Immunogenic assays may also be used in the present invention to determine the presence of Leishmania infection in a patient or blood supply and evaluate the capability of a patient for generating an immune response. These assays include ELISA using sera or antibodies from a patient or experimental animal, delayed-type hypersensitivity, induction of cytokine expression and induction of proliferation.

In one aspect of this invention, methods are disclosed for determining the presence of Leishmania infection in patients and blood supplies by detecting antibodies to Lt-210. In general, Leishmania infection may be detected in any biological sample that contains antibodies. Preferably, the sample is whole blood, serum, plasma, saliva, cerebrospinal fluid, or urine. More preferably, the sample is a blood or serum sample obtained from a patient or a blood supply. Briefly, Leishmania infection may be detected using one or more polypeptides containing one or more of the epitopes discussed above, or variants thereof. If multiple epitopes are employed, these epitopes may be present on one or more polypeptides. The polypeptide or polypeptides are then used to determine the presence or absence of reactive antibodies in the sample, relative to a predetermined cut-off value.

There are a variety of assay formats known to those of ordinary skill in the art for using a polypeptide to detect antibodies in a sample. See, e.g., Harlow and Lane, *Antibodies: A Laboratory Manual*, Cold Spring Harbor Laboratory, 1988, which is incorporated herein by reference. In a preferred embodiment, the assay involves the use of polypeptide immobilized on a solid support to bind to the antibody in the sample. Bound antibody may then be detected using a detection reagent containing a reporter group conjugated to a binding agent that binds to the antibody/peptide complex. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized polypeptide after incubation of the polypeptide with the sample. The extent to which components of the sample inhibit the binding of the labeled antibody to the polypeptide is indicative of the reactivity of the sample with the immobilized polypeptide.

The solid support may be any material known to those of ordinary skill in the art to which the polypeptide may be attached. For example, the support may be a test well in a microtiter plate or nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptide may be bound to the solid support by any of the various techniques known to those in the art. These techniques are amply described in the patent and scientific literature. The binding may be by noncovalent association, such as adsorption, or covalent attachment. Covalent attachment may be accomplished by a direct linkage between the antigen and functional groups on the support or by way of a cross-linking agent. Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 $\mu$g to about 1 $\mu$g, and preferably about 100 $\mu$g, is sufficient to bind an adequate amount of antigen. Nitrocellulose binds approximately 100 $\mu$g of protein per $cm^3$.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to a support having an appropriate polymer coating using benzoquinone or by condensation of an aldehyde group on the support with an amine and an active hydrogen on the polypeptide (see, e.g., Pierce Immunotechnology Catalog and Handbook (1991) at A12-A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Sample containing unbound antibodies is then removed from the immobilized polypeptide, and a detection reagent capable of binding to the immobilized antibody-polypeptide complex is added. The amount of detection reagent that remains bound to the solid support is then determined using a method appropriate for the specific detection reagent.

Once the polypeptide is immobilized on the support, the remaining protein binding sites on the support are typically blocked. Any suitable blocking agent known to those of ordinary skill in the art, such as bovine serum albumin (BSA), non-fat dry milk, or Tween 20™ (Sigma Chemical Co., St. Louis, Mo.) may be employed. The immobilized polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to permit detect the presence of antibody within a Leishmania-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound antibodies may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, ant-immunoglobulin, lectin, avidin, or free polypeptide) conjugated to a reporter group. Preferred reporter groups include enzymes, such as horseradish peroxidase, substrates, cofactors, inhibitors, dyes, radioisotopes, luminescent molecules, fluorescent molecules and biotin. The conjugation of binding agent to reporter group may be achieved using standard methods known to those of ordinary skill in the art. Common binding agents may also be purchased conjugated to a variety of reporter groups (e.g., Zymed Laboratories, San Francisco, Calif. and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed, and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent molecules and fluorescent molecules. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-Leishmania antibodies in the sample, the signal detected from the reporter group that remains bound to the solid support is generally compared to a signal that corresponds to a predetermined cut-off value. In one preferred embodiment, the cut-off value is preferably the average mean signal obtained when the immobilized polypeptide is incubated with samples from an uninfected patient. In general, a sample generating a signal that is three standard deviations above the predetermined cut-off value is considered positive (i.e., reactive with the polypeptide). In an alternate preferred embodiment, the cut-off value is determined using a Receiver Operator Curve, according to the method of Sackett et al., *Clinical Epidemiology.: A Basic Science for Clinical Medicine*, p. 106–7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate.

In a related embodiment, the assay is performed in a flow-through or strip test format, wherein the antigen is immobilized on a membrane such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of Leishmania antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 $\mu$g to about 1 $\mu$g, and more preferably from about 50 $\mu$g to about 500 $\mu$g. Such tests can typically be performed with a very small amount (e.g., one drop) of patient serum or blood.

In another aspect, the presence of Leishmania infection is determined by a delayed-type hypersensitivity (DTH) reaction. DTH is performed by injecting the polypeptide intradermally into the skin of a patient who may be infected with Leishmania. The cell-mediated immunity reaction is characterized by erythema and induration which appears only after several hours and reaches a maximum at 48–72 hours, thereafter subsiding. From 1 to 50 $\mu$g of protein is injected intradermally in 100 $\mu$l volume. Induration is measured at 48–72 hours. A positive reaction is considered to be greater than 5 mm induration. The preferred polypeptide used in a DTH assay contains at least 20 amino acids of non-repeat sequence. It may include all or a portion of the non-repeat or repeat sequence of Lt-210. The portion of the non-repeat sequence that is optimal in eliciting a DTH reaction may be determined by synthesis of polypeptides by the methods discussed above and tested in patients with known *L. tropica* infections or alternatively tested in experimental animals infected with *L. tropica*, such as mice. In mice, a DTH assay may be performed by administering the antigen in the ears or foot pads and measuring subsequent swelling. Measurable swelling of 0.1–5 mm at 24–48 hours is indicative of positive DTH reaction. Confirmation may be made by a histological examination; in DTH, the injection site is infiltrated by mononuclear cells.

In other aspects of the invention, other assays such as a proliferation assay or production of cytokines, may be utilized to establish the capability of a patient to generate an immune response to Leishmania. Briefly, such an evaluation may be performed by contacting a biological sample, preferably peripheral blood mononuclear cells (PBMC), obtained from the patient, who may be infected or uninfected, with a polypeptide of this invention, and measuring a suitable activity of the cells. PBMCs for this purpose may be isolated by methods known to those in the art, including by density centrifugation through, for example, Ficoll™ (Winthrop Laboratories, New York). In general, the amount of polypeptide that is sufficient for evaluation of about $10^4$–$10^6$ cells ranges from about 1 $\mu$g/ml to about 50 $\mu$g/ml, and preferably is about 10 $\mu$g/ml. Incubation of polypeptide with PBMCs is typically performed at 37° C. for about five days. Following incubation with polypeptide, the PBMCs are assayed for a suitable activity. For example, the activity measured may be a proliferative response, which may be evaluated by methods known to those of ordinary skill in the art, such as exposing the cells to a pulse of radiolabeled thymidine and measuring the incorporation of label into cellular DNA. In general, a proliferative response where the stimulation index (i.e., the mean cpm of cells stimulated with antigen divided by the mean cpm of cells without antigen) is greater than or equal to 5 is indicative of a patient with a capacity for generating an immune response. Alternatively, the response measured may be the secretion of cytokines, such as IFN-γIL-2, IL-12p70, IL-12p40 subunit, or IL-1. In particular, IFN-8 production is indicative of stimulation of T cells, and Th1 cells in particular, that are responsible for the protective effect against Leishmania. The level of mRNA encoding IFN-γ or any of these other cytokines, may be determined by techniques well known to those of ordinary skill in the art (which include amplification by polymerase chain reaction (PCR), Northern blotting and RNase probe protection). High levels of cytokine secretion or mRNA expression correspond to a superior capacity for generating an immune response. In general, a patient has a lowered ability to generate an immune response if IFN-γ or mRNA encoding IFN-γ cannot be detected (by the methods disclosed herein) in PBMCs treated with a Lt-210 polypeptide, such as recombinant Lt-1 polypeptide.

Cytokine production is conveniently measured by a capture ELISA. Briefly, by way of example, a monoclonal anti-human IFN-γ antibody is used to coat an ELISA plate. Following a wash, culture supernatants collected 72 hours after stimulation of PBMC with recombinant Lt-1 polypeptide were added to the wells. Following washes, a polyclonal anti-human IFN-γ antisera is added and incubated in the wells. An appropriate secondary antibody conjugated to horseradish peroxidase is added followed by a developing reagent, such as ABTS. The level of IFN-γ production that indicates the capacity of a patient to generate an immune response is 30 pg/ml to 20 ng/ml.

In other aspects of this invention, antibodies to polypeptides derived from Lt-210 are provided. Either polyclonal antibodies or monoclonal antibodies may be raised and used. Monoclonal antibodies are preferred.

Monoclonals may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described herein. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies directed to the polypeptides described herein may be isolated from the supernatants of growing hybridoma colonies. In this process, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. One or more Lt-210 polypeptides may be used in the purification process, for example, in an affinity chromatography step.

Monospecific antibodies that bind to an Lt-210 polypeptide may be used, for example, to detect Leishmania infection in a biological sample using one of a variety of immunoassays, which may be direct or competitive. Briefly, in one direct assay format, a monospecific antibody may be immobilized on a solid support (as described above) and contacted with the sample to be tested. After removal of the unbound sample, a second monospecific antibody, which has been labeled with a reporter group, may be added and used to detect bound antigen. In an exemplary competitive assay, the sample may be combined with the monoclonal or polyclonal antibody, which has been labeled with a suitable reporter group. The mixture of sample and antibody may then be combined with polypeptide antigen immobilized on a suitable solid support. Antibody that has not bound to an antigen in the sample is allowed to bind to the immobilized antigen, and the remainder of the sample and antibody is removed. The level of antibody bound to the solid support is inversely related to the level of antigen in the sample. Thus, a lower level of antibody bound to the solid support indicates the presence of Leishmania in the sample. Other formats for using monospecific antibodies to detect Leishmania in a sample will be apparent to those of ordinary skill in the art, and the above formats are provided solely for exemplary purposes. Polyclonal antibodies may be raised in experimental animals, such as rats, mice, or rabbits. Sera from the animals may be used directly or the immunoglobulin fraction or antibodies specific for the immunogenic polypeptide may be purified by techniques well known in the art (see Harlow and Lane, Antibodies: A laboratory manual, Cold Spring Harbor Laboratory, 1988). Polyclonal antibodies may be used in place of monospecific antibodies as described above.

In another aspect of this invention, vaccines and pharmaceutical compositions are provided for the prevention of Leishmania infection, and complications thereof, in a mammal, preferably a human or dog. Pharmaceutical compositions generally comprise one or more polypeptides, containing one or more epitopes of Leishmania proteins, and a physiologically acceptable carrier. The vaccines comprise one or more of the above polypeptides and optionally, an adjuvant, for enhancement of the protective immune response.

Routes and frequency of administration and polypeptide doses will vary from individual to individual and may parallel those currently being used in immunization against other protozoan infections. In general, the pharmaceutical compositions and vaccines may be administered by injection (e.g., intramuscular, intravenous or subcutaneous), intranasally (e.g., by aspiration) or orally. Between 1 and 4 doses may be administered for a 2–6 week period. Preferably, two doses are administered, with the second dose 2–4 weeks later than the first. A suitable dose is an amount of polypeptide that is effective to raise antibodies in a treated mammal that are sufficient to protect the mammal from Leishmania infection for a period of time. In general, the amount of polypeptide present in a dose ranges from about 1 pg to about 100 mg per kg of host, typically from about 10 pg to about 1 mg, and preferably from about 100 pg to about 1 $\mu$g. Suitable dose sizes will vary with the size of the animal, but will typically range from about 0.01 mL to about 5 mL for 10–60 kg animal.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

It will also be evident that, although specific embodiments of the invention have been described herein for purposes of illustration, various modifications may be made without deviating from the spirit and scope of the invention.

EXAMPLE 1

Isolation and Characterization of Clones Encoding Lt-210

Briefly, an expression library was constructed from *L. tropica* genomic DNA and screened with sera isolated from VTL patients. Three clones, Lt-1, Lt-2, and Lt-3, containing a portion of the Lt-210 gene were identified and purified.

Sera from VTL patients were received from Drs. M. Grogl and A. Magill. The VTL patient group included eight individuals from whom parasites were isolated and cultured, seven of which had confirmed infection with *L. tropica*. Four other patients were culture negative, but were still considered to be infected based on either PCR analysis or a positive monoclonal antibody smear (Dr. Max Grogl, personal communication). Normal sera were received from the American Red Cross, Portland, Oreg.

*L. tropica* (MHOM/SA/91/WR1063C) genomic DNA was isolated by solubilizing *L. tropica* promastigotes in 10 mM Trs-HCl, ph 8.3, 50 mM EDTA, 1% SDS and treating with 100 μg/ml RNaseA and 100 μg/ml proteinase K. The sample was then sequentially extracted with an equal volume of phenol, phenol:chloroform (1:1), and Chloroform. DNA was precipitated by adding 0.1 volume of 3 M sodium acetate (pH 5.2) and 2.5 volume 95% ethanol. The precipitate was resuspended in 10 μM Tris, 1 mM EDTA. DNA was sheared by passage through a 30-gauge needle to a size range of 2–6 kilobase. Briefly, sheared genomic DNA was repaired by incubation with DNA poll in the presence of 100 μM each dATP, dCTP, dGTP, and dTTP. EcoRI adapters were ligated to the DNA fragments. After removal of unligated adapters by passage over a G-25 Sephadex™ column, the fragments were inserted in EcoRI cut Lambda ZAPII (Stratagene, La Jolla, Calif.). Approximately 43,000 pfu were plated and screened.

For immunological screening of the *L. tropica* library, serum samples from the 11 infected patients described above were pooled and anti-*E. coli* reactivity removed by affinity chromatography (Sambrook et al., supra, p. 12.27–12.28). Lambda phage expressing reactive proteins were detected after antibody binding by protein A-horseradish peroxidase and ABTS substrate. Three positive clones, called Lt-1, and Lt-2, and Lt-3, were isolated. The clones ranged in size from 1.4 to 3.3 kb and encoded polypeptides of 75 kD, 70 kD, and 120 kD, respectively. These three clones contain partial sequences of the Lt-210 gene. Lt-1 and Lt-2 are overlapping clones and were chosen for further study.

The DNA sequences of Lt-1 and Lt-2 were determined. Exonuclease III digestion was used to create overlapping deletions of the clones (Heinikoff, *Gene* 28:351–359, 1984). Single strand template was prepared and the sequence determined with Applied Biosystems Automated Sequencer model 373A or by Sanger dideoxy sequencing (13). The sequence on both strands of the coding portion of Lt-1 clone was determined. The partial sequence of one strand of Lt-2 clone was determined.

FIG. 1A presents the DNA sequence of Lt-1 and the predicted amino acid sequence of the open reading frame. The DNA sequence of the coding portion of the Lt-1 clone (FIG. 1A) includes a repeated nucleotide sequence at the 5' portion of the clone containing eight copies of a 99 bp repeat, three copies of a 60 bp repeat unit, which is part of the larger 99 bp repeat, and 800 bp of non-repeat sequence. The deduced amino acid sequence of the 99 bp repeat contains limited degeneracies (FIG. 1B). The mass of the predicted recombinant protein is 67,060 Daltons. A database search of PIR with the predicted amino acid sequence of the open reading frame yielded no significant homology to previously submitted sequences. Predicted secondary structure of the repeat portion of the clone is entirely α-helical.

Sequence analysis of Lt-2 revealed that the 3' portion of the clone consisted of a mixture of 60 and 99 bp repeats that were identical, excepting occasional degeneracies, to the 60 and 99 bp repeats observed in Lt-1. Collectively, the sequencing data suggest that Lt-1 and Lt-2 are different portions of the same gene, Lt-2 being upstream of Lt-1, with possibly a small overlap.

Hybridization analysis confirmed that rLt-2 and rLt-1 contain overlapping sequences. Genomic DNAs of various Leishmania species were restricted with a variety of enzymes, separated by agarose gel electrophoresis, and blotted on Nytran membrane filter (Scheicher & Schuell, Keene, N.H.). Inserts from rLt-1 and rLt-2 were labeled with $^{32}$P-CTP by reverse transcriptase from random oligonucleotide primers and used as probes after separation from unincorporated nucleotides on a Sephadex G-50 column. Hybridizations using the rLt-1 or the rLt-2 probe are performed in 0.2 M $NaH_2PO_4$/3.6 M NaCl at 65° C., whereas hybridization using the rLt-1r probe is performed in 0.2 M $NaH_2PO_4$/3.6 M NaCl/0.2 M EDTA at 60° C. overnight. Filters are washed in 0.075 M NaCl/0.0075 M sodium citrate pH 7.0 (0.15 M NaCl/0.0150 M sodium citrate for the Lt-1r probe), plus 0.5% SDS at the same temperature as hybridization.

Genomic DNA from a number of Leishmania species including *L. tropica* were analyzed by Southern blots as described above using the Lt-1, Lt-2, and Lt-1r inserts separately as probes. Collectively, various digests of *L. tropica* DNA indicate that this gene has a low copy number (FIG. 2). A similar, overlapping pattern was observed using either the Lt-1 or Lt-2 insert as a probe (FIG. 2), consistent with the premise that these two clones contain sequences near or overlapping one another. In addition, sequences hybridizing with these clones are present in other Leishmania species.

Figure 3:
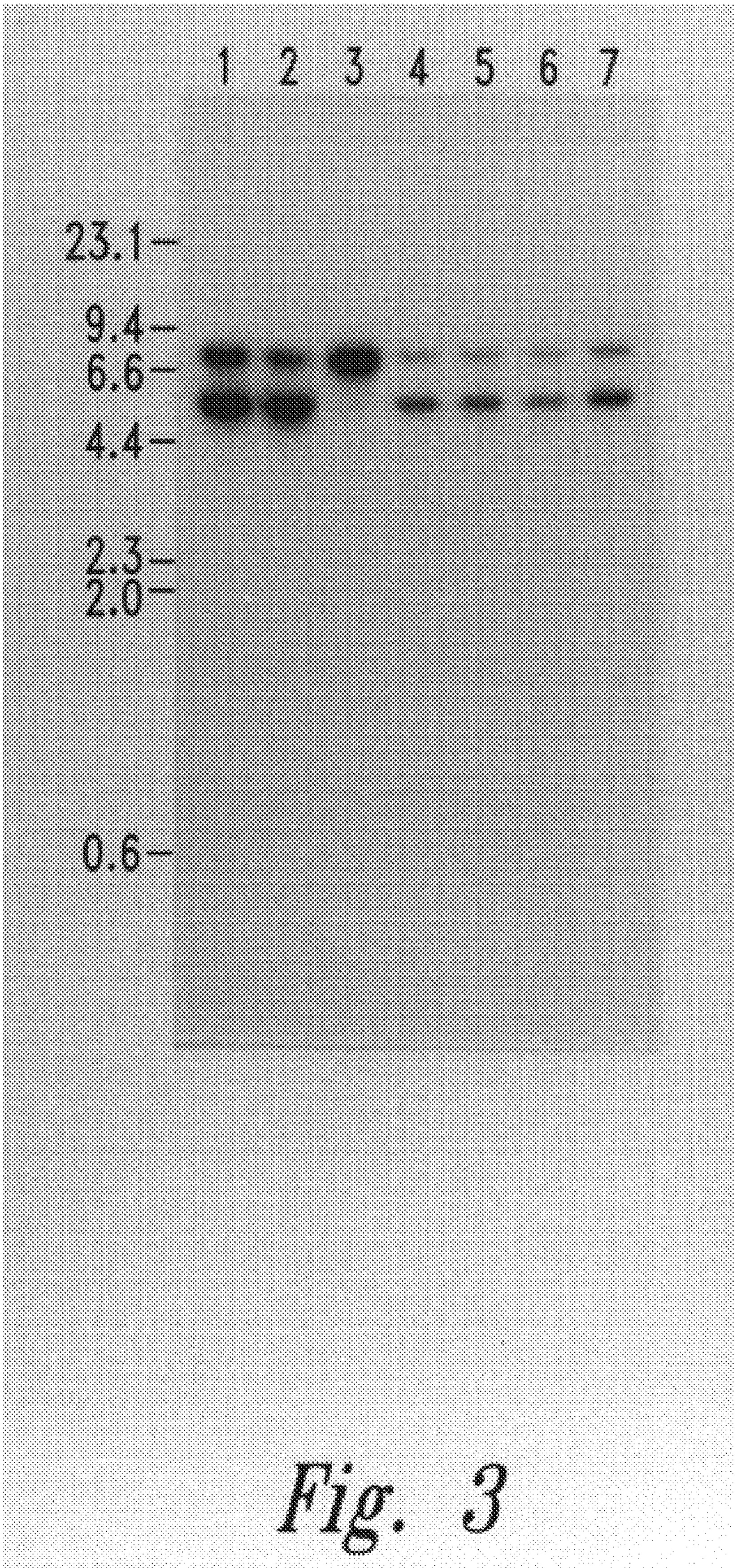
FIG. 3 is a Southern blot analysis of fragments containing the Lt-1r sequence, a representative fragment containing at least one repeat sequence of Lt-210. Lt-1r was used as a probe on a blot containing Pst I digests of genomic DNA of *L. tropica* isolated from VTL patients (lanes 1, 3, 4, 5) and *L. tropica* isolated from CL patients (lanes 2, 6, 7).

*L. tropica* isolates have limited heterogeneity. Southern analyses of digested genomic DNA from four *L. tropica* parasite strains isolated from VTL patients and three *L. tropica* parasite strains isolated from CL cases (two human, one canine) were performed. The Lt-1r insert was labeled and used as a probe. The seven different *L. tropica* isolates yielded similar intensities and restriction patterns, with only a single restriction fragment length polymorphism among the isolates (FIG. 3). These data, along with Southern analyses with additional enzymes, indicate limited heterogeneity in this region among the *L. tropica* isolates.

The recombinant proteins of Lt-1 and Lt-2 were expressed and purified. The nested deletion set of Lt-1 formed for sequencing included a clone referred to as Lt-1r, which contains one and one-third repeats. This polypeptide was also expressed and purified. In vivo excision of the pBluescript SK$^-$ phagemid from Lambda Zap II was performed according to the manufacturer's protocol. Phagemid virus particles were used to infect *E. coli* XL-1 Blue. Production of protein was induced by the addition of IPTG. Protein was recovered by first lysing pellets of induced bacteria in buffer (LB, 50 mM Tris-HCl, pH 8.0, 100 mM NaCl, 10 mM EDTA) using a combination of lysosyme (750 μg/mL) and sonication. rLt-1, rLt-2, and rLt-1r, were recovered from the inclusion bodies after solubilization in 8 M urea (rLt-1 and rLt-2) or 4 M urea (rLt-1r. Proteins rLt-1 and rLt-2 were enriched and separated by precipitation with 25%–40% ammonium sulfate and rLt-1r was enriched by precipitation with 10%–25% ammonium sulfate. The proteins were further purified by preparative gel electrophoresis in 10% SDS-PAGE. Recombinant proteins were eluted from the gels and dialyzed in phosphate-buffered saline (PBS). Concentration was measured by the Pierce (Rockford, Ill.) BCA assay, and purity assessed by Coomassie blue staining after SDS-PAGE.

EXAMPLE 2

Identification of LT-210 Protein in Leishmania

Rabbit antiserum to rLt-1 was raised in an adult New Zealand White Rabbit (R & R Rabbitry, Stanwood, Wash.). The rabbit was primed with an initial subcutaneous (s.c.) delivery of 200 μg of muramyl dipeptide (Calbiochem, La Jolla, Calif.). Two successive s.c. immunizations of 100 μg rLt-1 in 1 ml IFA were administered at three week intervals followed by a final i.v. boost of 25 μg rLt-1 four weeks later. Serum was collected two weeks following the final injection.

The rabbit antiserum was used on an immunoblot of Leishmania lysates. Crude lysate of Leishmania parasites, purified rLt-1, and purified rLt-1r were electrophoresed in 7.5% or 12% SDS-PAGE. The proteins were electroblotted onto nitrocellulose filters (15 minutes at 50 V followed by 1 hour at 100 V). Filters were prepared by blocking with 5% nonfat milk in PBS at 4° C. overnight and washed 3 times in PBS/0.1% Tween-20. The filter was probed for 1 hour at room temperature with human sera (diluted 1:50 in PBS/0.1% Tween-20) or rabbit sera (diluted 1:250 in PBS/0.1% Tween-20) on a rocker platform. Filters were subsequently washed 3 times with PBS/0.1% Tween-20. $10^5$ cpm/ml $^{125}$I-labeled protein A was added. Bound antibody was detected by autoradiography.

Figure 4:
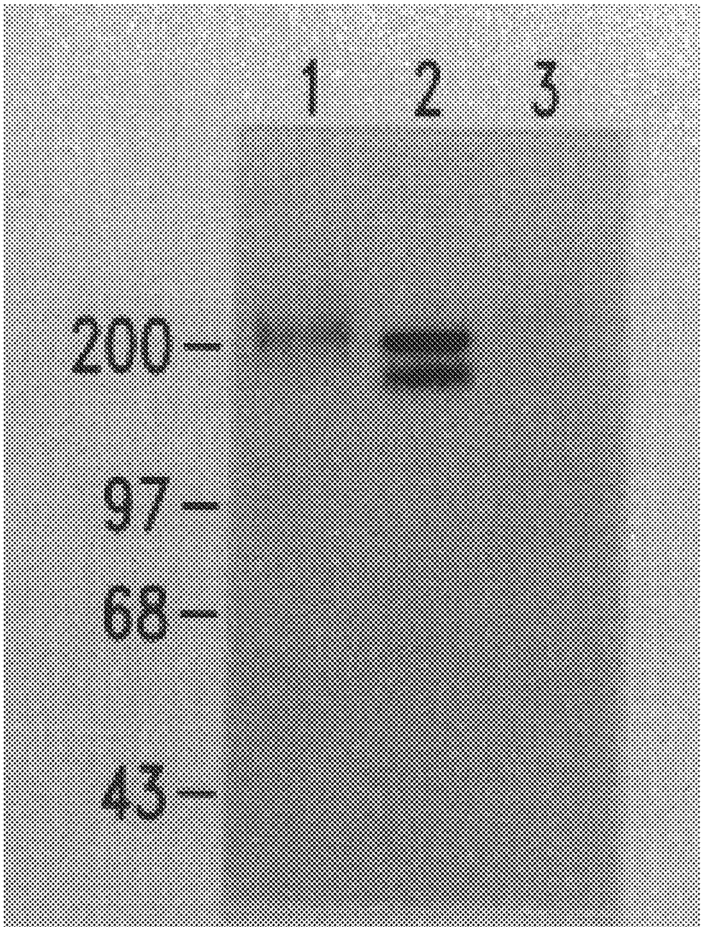
FIG. 4 is an immunoblot showing reactivity of rabbit anti-rLt-1 sera on Leishmania lysates. Lysates from *L. major* promastigotes (lane 1), *L. major* amastigotes (lane 2) and *L. tropica* promastigotes (lane 3) were electrophoresed by SDS-PAGE and transferred to nitrocellulose. The blots were reacted with 1:250 dilution of rabbit anti-rLt-1 sera.

As can be seen in FIG. 4, antibody reactivity to a 210 Kd protein in *L. tropica* promastigote lysate (lane 3) was observed. Due to the great difficulty of obtaining *L. tropica* amastigotes, the reactivity of anti-rLt-1 antisera with *L. major* promastigote and amastigote lysates was examined. As seen in lanes 1 and 2 a cross-reactive protein of similar size in *L. major* is most abundant in amastigotes, the predominant form during human infection.

EXAMPLE 3

Elisa Assay to Detect Leishmania Infection

Microassay plates (#3915, Falcon, Lincoln Park, N.J.) are coated with recombinant antigen or parasite lysate in coating buffer (15 mM $Na_2HCO_3$/28 mM $NaH_2CO_3$, pH 9.6) and incubated either overnight at 4° C. or 1 hour at 37° C. Plates are subsequently blocked 1 hour with PBS/1% Tween-20 and washed 5 times with PBS/0.1% Tween-20 (PBS-T). Sera are added (50 $\mu$l of 1:50 dilution) and incubated 30 minutes at room temperature on a shaker. In competition experiments, sera are pre-incubated for 30 minutes with 5 $\mu$g of rLt-1r at room temperature. Following 5 washes with PBS-T, bound antibodies are detected with protein A horseradish peroxidase (Zymed, San Francisco, Calif.) and ABTS substrate as previously described (Reed et al., *Am. J. Trop. Med. Hyg.* 43:632–639, 1990). Absorbance values are reported relative to the mean of 5 control sera. Two sample t-test was used in statistical analysis.

Figure 5:
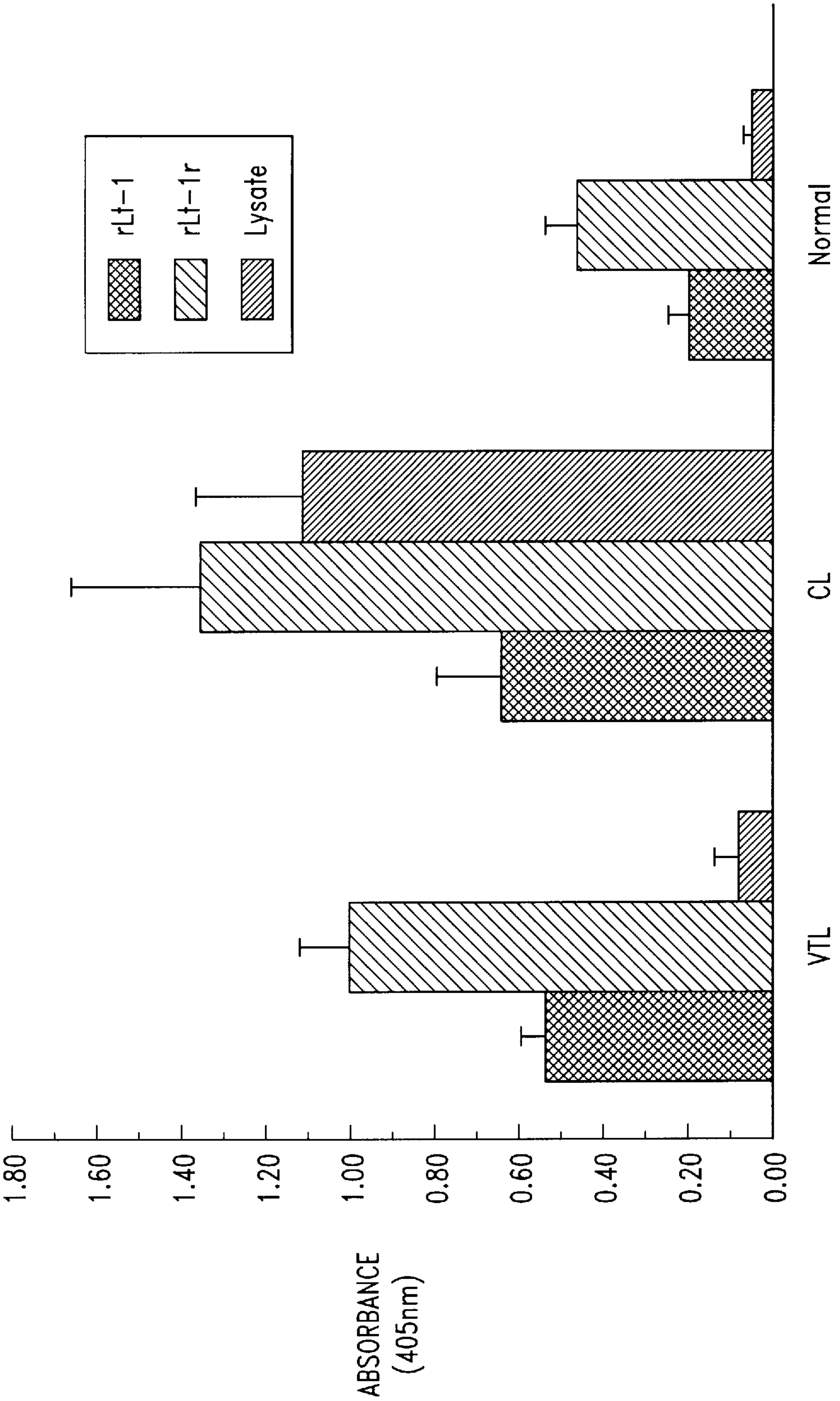
FIG. 5 is a graph depicting results of ELISA evaluation of VTL patient sera and CL patient sera using *L. tropica* lysate and the recombinant antigens, rLt-1 and rLt-1r. Absorbance values (mean+SE) are shown for sera isolated from VTL patients (n=12), CL patient (n=10) and normal (n=18).

Both rLt-1 and rLt-1r were evaluated by ELISA using sera from the following groups: VTL patients, CL patients, and normal sera (N) (FIG. 5). Mean reactivity to rLt-1 was significantly higher in both the CL group (p=0.002) and the VTL group (p<0.001) compared to normal sera. A significant increase in mean reactivity to rLt-1r was also observed in both the CL group (p=0.001) and the VTL group (p<0.001) relative to normal sera. In addition, a significant increase in reactivity to rLt-2 was observed in the VTL group (p=0.036) but not in the CL group (p=0.279) compared to normal sera (data not shown). Mean reactivity to *L. tropica* promastigote lysate was significantly increased in the CL group (p<0.001), but not in the VTL group (p=0.594), compared to normals.

To determine the complexity of epitopes being recognized by patient sera, two VTL sera and one CL sera were pre-incubated with 5 $\mu$g of rLt-1r and tested for reactivity with the rLt-1 antigen in an ELISA assay. In all three cases, the reactivity to rLt-1 was eliminated by pre-incubation with rLt-1r (data not shown), indicating that these individuals were reacting exclusively to epitopes contained within the repeated sequence.

The reactivity of patient sera was further examined by ELISA using IgG subclass specific monoclonal antibodies. For determination of IgG subclasses, ELISA plates were coated, blocked, and incubated with sera as described above. Plates were washed 5 times with PBS-T. Mouse anti-human IgG1 monoclonal antibody (Mab) (Calbiochem, La Jolla, Calif.), mouse anti-human IgG2 Mab (Calbiochem, La Jolla, Calif.), mouse anti-human IgG3 Mab (Calbiochem, La Jolla, Calif.) or mouse anti-human IgG4 Mab (Calbiochem, La Jolla, Calif.) was added (50 ul of a 1:1000 dilution), and plates were washed 5 times with PBS-T. Bound antibodies were detected by goat anti-mouse IgG1- horseradish peroxidase (Zymed, San Francisco, Calif.; 1:500 dilution) and ABTS substrate.

Figure 7A:
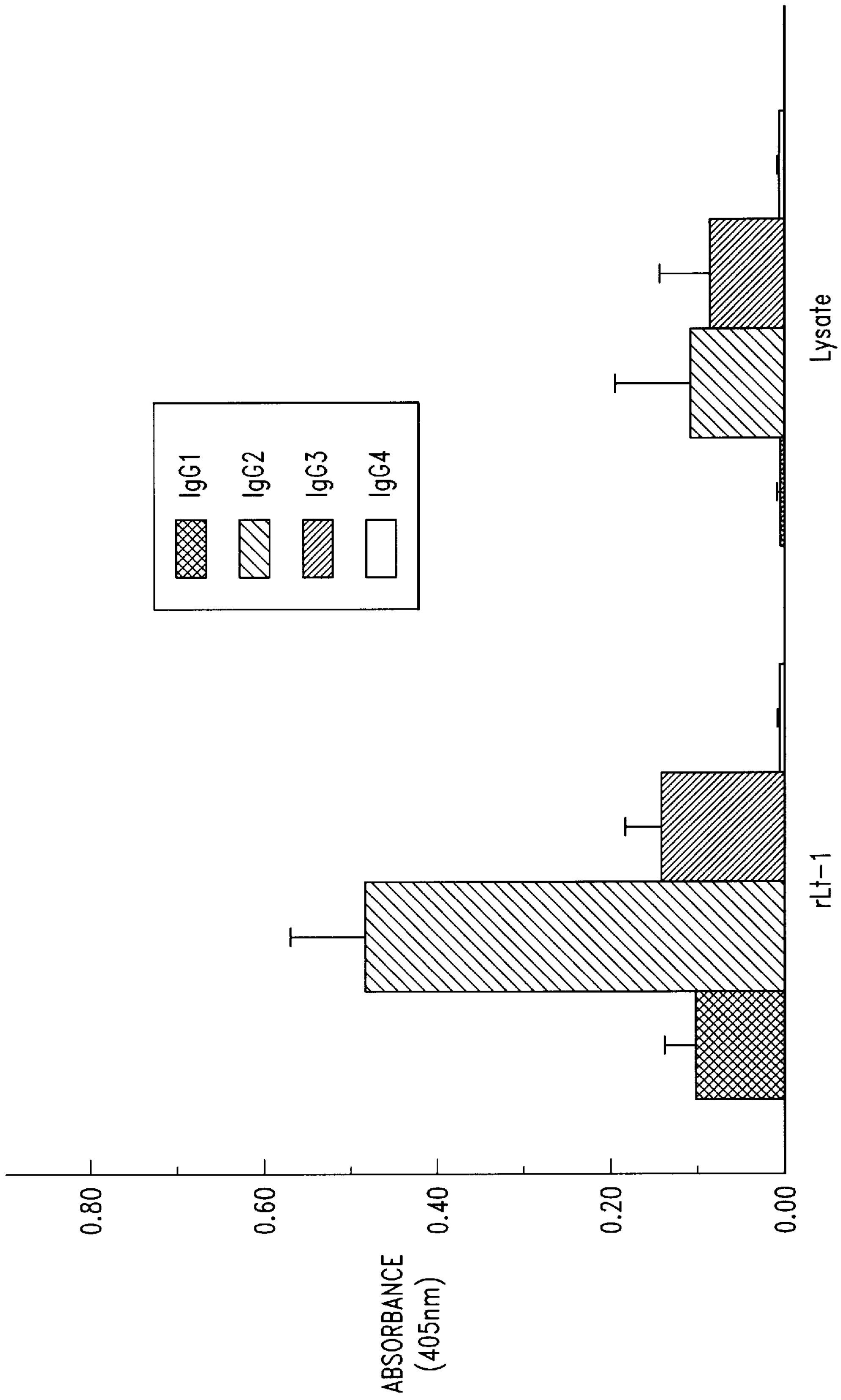
FIG. 7 contains graphs from ELISAs examining IgG subclass reactivity of VTL patient sera (A) and CL patient sera (B) to *L. tropica* lysate or rLt-1 protein. Absorbance values (mean+SE) are shown for VTL patient sera (n=11) and CL patient sera (n=10).
Figure 7B:
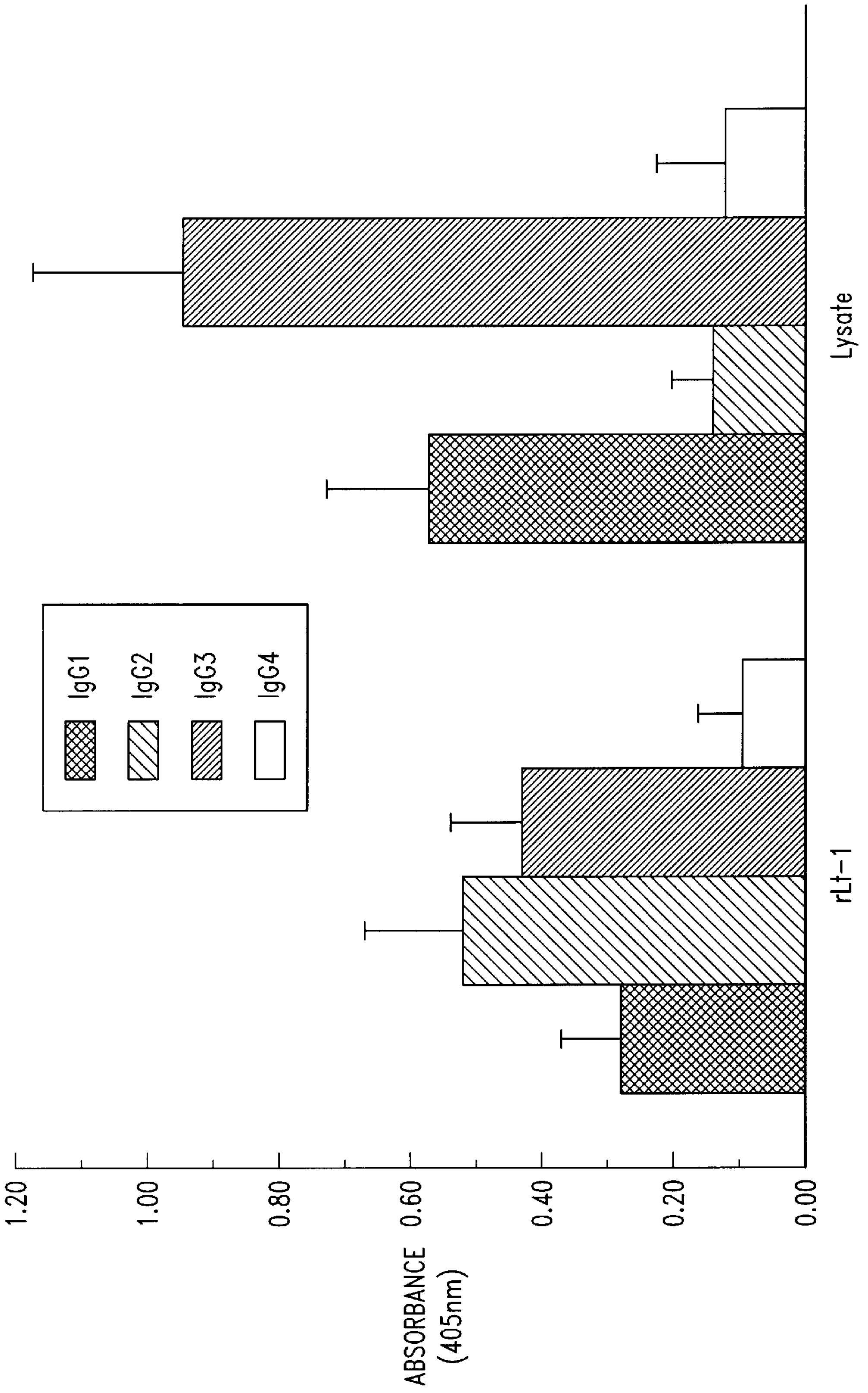

The results of these studies (FIG. 7) indicate a more restricted serological response to the recombinant antigen rLt-1 by VTL patients than was observed with CL patients. While approximately equivalent mean reactivities were observed for IgG2 subclass with the recombinant rLt-1 in both CL and VTL patient sera, reactivities with IgG1 and IgG3 subclasses were increased in Cl patients. In addition, the subclass reactivity of CL sera to *L. tropica* lysate was biased more towards IgG1 and IgG3 than was observed with Cl sera to rLt-1. Normal mean reactivities, when measurable, were biased toward IgG1 and IgG2 (data not shown). Similar results were obtained for the rLt-1r antigen (data not shown).

EXAMPLE 4

Immunoblot Assay to Detect Leishmania Infection

Figures 6A, 6B, 6C, 6D:
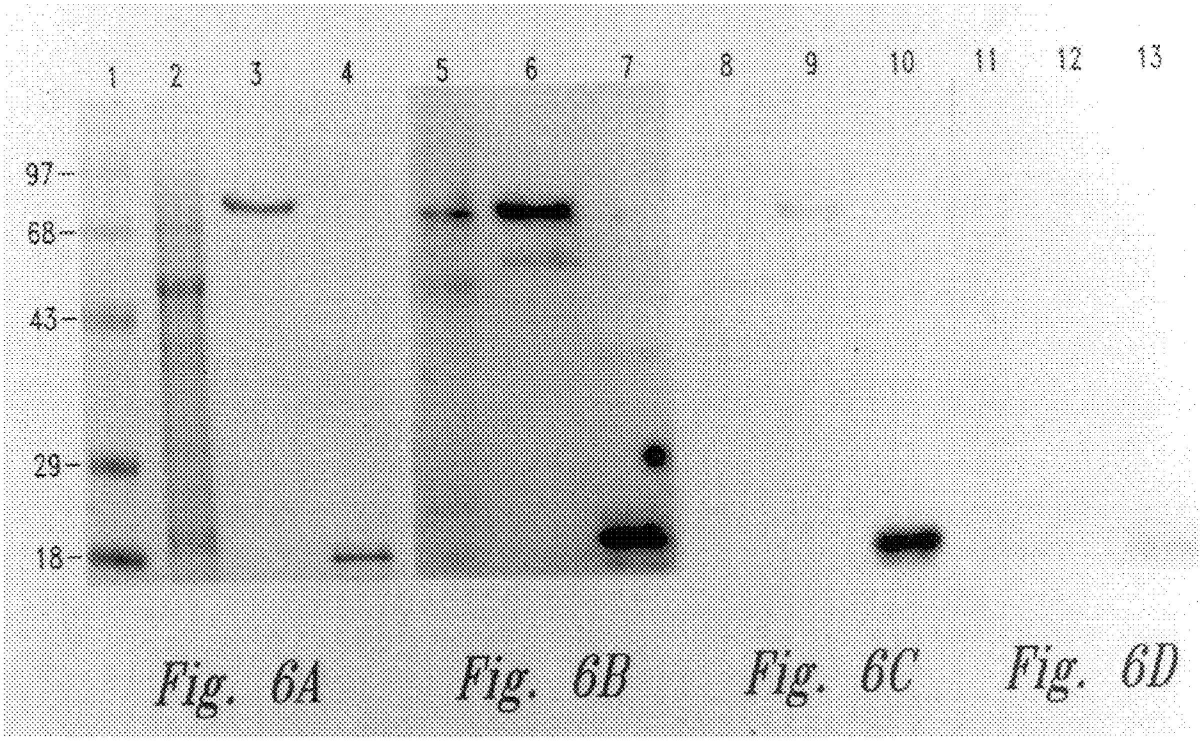
FIG. 6 is an immunoblot analysis of *L. tropica* lysate, rLt-1, and rLt-1r. *L. tropica* lysate, rLt-1 protein, and rLt-1r protein were electrophoresed and transferred to nitrocellulose. Blots were either strained with Coomassie blue (lanes 2–4), reacted with two different VTL patient sera (lanes 5–7, 8–10), or reacted with a pool of normal sera (n=3, lanes 11–13). Molecular markers are shown in lane 1.

Immunoblot analysis was performed as described above with parasite lysate, rLt-1, and rLt-1r, using sera from two VTL patients and a pool of three normal sera (FIG. 6). Increased reactivity to both purified recombinant antigens was observed in the VTL patients compared to normals. Collectively, the ELISA and immunoblot data indicate that both the rLt-1 and rLt-1r antigens are more immunogenic than promastigote lysate.

EXAMPLE 5

Peripheral Blood Mononuclear Cell Response to LT-1

Patient and normal PBMC were analyzed for proliferation and production of the cytokine IFN-γ in response to either *L. tropica* lysate or purified Lt-1 polypeptide.

Proliferative assays are performed using PBMC. PBMC are cultured at $2\times10^6$ cells/ml in RPMI-1640 (endotoxin-free, less than 10 pg/ml) supplemented with endotoxin free 10% fetal bovine serum. Recombinant rLt-1 or parasite lysate are added at 10 $\mu$g/ml for 5 days. Control cultures are not incubated with antigen. Cultures are then pulsed with 1 $\mu$Ci of $^3$H-thymidine and further incubated 18 hours before harvesting. Six patients and six normals were assayed for proliferation. No significant increase in the proliferative responses to either lysate or rLt-1 was observed in patient compared to normal PBMC.

Figure 8:
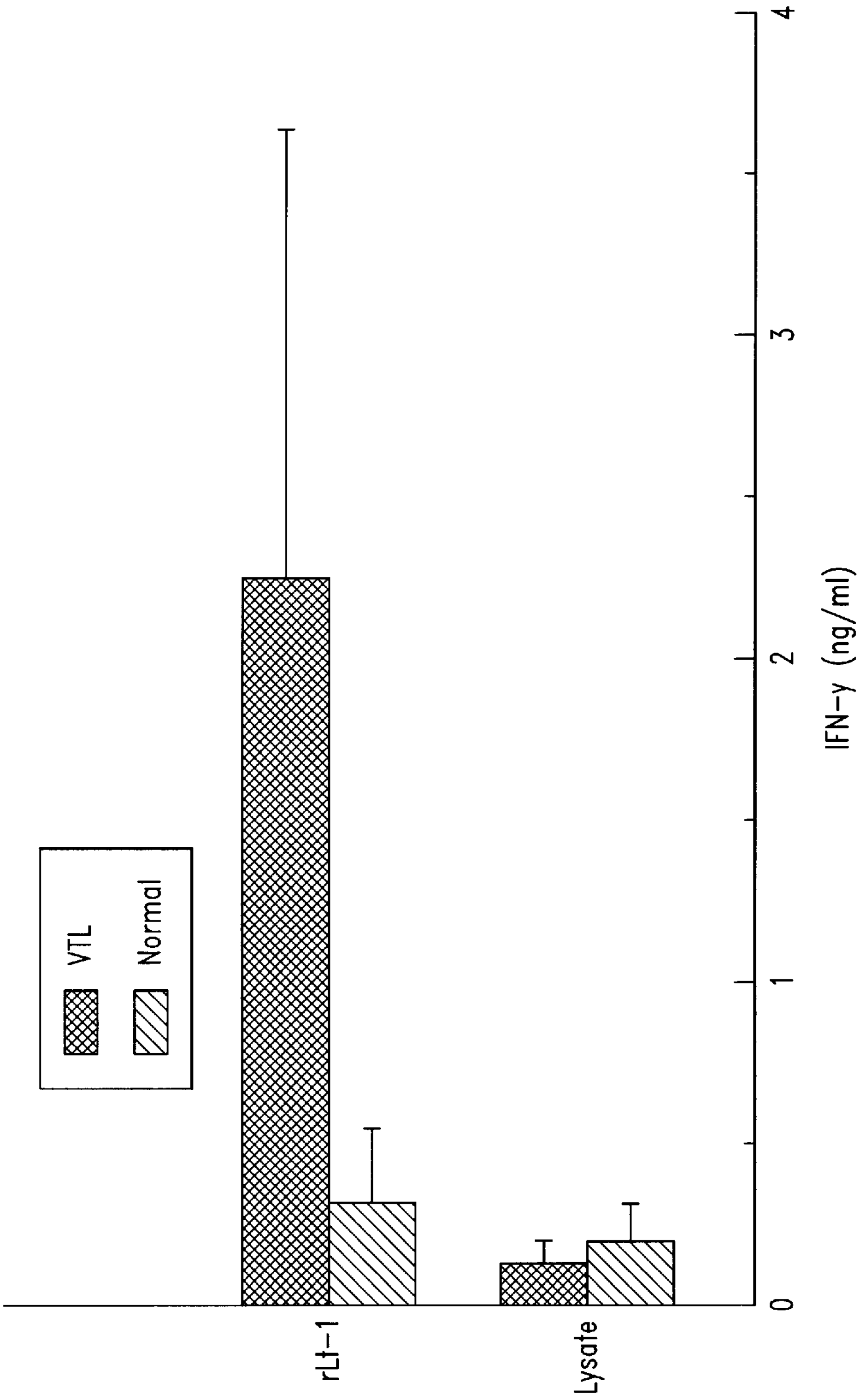
FIG. 8 is a graph showing stimulation of γ-IFN by VTL patient PBMC with rLt-1 protein. Production of γ-IFN (mean+SE) by VTL patient PBMC (n=5) and normal PBMC (n=4) in response to incubation with *L. tropica* lysate and recombinant antigen rLt-1 was determined in culture supernatants by ELISA analysis after 72 hour incubation.

Cytokine production of IFN-γ was measured by a double sandwich ELISA using mouse anti-human IFN-8 Mab (Chemicon, Temucula, Calif.) and polyclonal rabbit anti-human IFN-8 serum. A standard curve was generated using human IFN-8 (Genentech Inc., San Francisco, Calif.). rLt-1 but not promastigote lysate, elicited the production of IFN-γ from patient PBMC at nanogram levels (FIG. 8). Collectively, 11 VTL patient and 17 normal PBMC cultured with rLt-1 were assayed, and a significant increase in IFN-γ production was observed with patient PBMC (p=0.008). In contrast, neither *L. tropica* lysate or rLt-1 was able to elicit production of detectable levels of IL-4 in patients or normals. Similarly, rLt-1 was unable to elicit production of IL-10 or TNF-α production in patient or normal PBMC.

EXAMPLE 6

Delayed Type Hypersensitivity Assay

Delayed type hypersensitivity response is measured following the intradermal injection of polypeptide. From 0.1–50 μg of polypeptide is injected intradermally in 0.1 ml in the flex or surface of the forearm. The skin test area is observed for induration at 48–72 hours later. Induration 5 mm or greater is considered a positive reaction (Reed et al, *Am. J. Trop. Med Hyg.* 35:79–85, 1986).

From the foregoing, it will be evident that although specific embodiments of the invention have been described herein for the purpose of illustrating the invention, various modifications may be made without deviating from the spirit and scope of the invention.

What is claimed is:

1. An isolated polypeptide comprising at least one repeat sequence of a *L. tropica* Lt210 polypeptide having an amino acid sequence shown in SEQ ID NO: 2.

2. An isolated polypeptide having an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, and SEQ ID NO: 11.

3. An isolated polypeptide having an amino acid sequence shown in SEQ ID NO:4.

4. An isolated polypeptide comprising the amino acid sequence:

Gln-Ala-Arg-Xaa-Gln-Ala-Leu-Glu-Glu-Ala-Ala-Arg-Leu-Xbb-Ala-Glu-Leu-Glu-Xcc-Xcc-Glu-Glu-Ala-Ala-Arg-Leu-Xdd-Xee-Met-His-Xcc-Xff-Glu, (SEQ ID NO:3)

wherein Xaa is Val or Ser; Xbb is Arg or Cys; Xcc is Ala or Glu; Xdd is Asp or Glu; Xee is Val or Ala; and Xff is Ala or Gly.

5. An isolated polypeptide comprising an epitope bound by an antibody to a *L. tropica* Lt210 polypeptide.

6. An isolated polypeptide having an amino acid sequence shown in SEQ ID NO:2.

7. An isolated *L. tropica* Lt210 polypeptide or an immunogenic variant thereof, the Lt210 polypeptide having an amino acid sequence shown in SEQ ID NO: 2.

8. A diagnostic kit for identifying a patient infected with *L. tropica*, comprising:

(a) a polypeptide according to any one of claims 1–6; and (b) a detection reagent.

9. The diagnostic kit of claim 8 wherein the polypeptide is bound to a solid support.

10. The diagnostic kit of claim 9 wherein the solid support is selected from the group consisting of nitrocellulose, latex and a plastic material.

11. The diagnostic kit of claim 8 wherein the detection reagent comprises a reporter group conjugated to a binding agent.

12. The diagnostic kit of claim 11 wherein the binding agent is selected from the group consisting of anti-immunoglobulin, protein A, protein G, lectins and avidin.

13. The diagnostic kit of claim 11 wherein the reporter group is selected from the group consisting of radioisotopes, fluorescent molecules, luminescent molecules, enzymes, biotin and dye particles.

* * * * *

```
                              SEQUENCE LISTING


(1) GENERAL INFORMATION:

   (iii) NUMBER OF SEQUENCES: 11


(2) INFORMATION FOR SEQ ID NO:1:

     (i) SEQUENCE CHARACTERISTICS:
          (A) LENGTH: 1771 base pairs
          (B) TYPE: nucleic acid
          (C) STRANDEDNESS: single
          (D) TOPOLOGY: linear

    (ix) FEATURE:
          (A) NAME/KEY: CDS
          (B) LOCATION: 1..1698

        (xi) SEQUENCE DESCRIPTION: SEQ ID NO:1:

CAG GCC CGC GTC CAG GCC CTC GAG GAG GCA GCG CGT CTC CGC GCG GAG        48
Gln Ala Arg Val Gln Ala Leu Glu Glu Ala Ala Arg Leu Arg Ala Glu
  1               5                  10                  15

CTG GAG GCG GCC GAG GAG GCG GCC CGC CTG GAT GTC ATG CAT GCG GCC        96
Leu Glu Ala Ala Glu Glu Ala Ala Arg Leu Asp Val Met His Ala Ala
             20                  25                  30

GAG CAG GCC CGT GTC CAG GCC CTC GAG GAG GCA GCG CGT CTC CGC GCG       144
Glu Gln Ala Arg Val Gln Ala Leu Glu Glu Ala Ala Arg Leu Arg Ala
         35                  40                  45

GAG CTG GAG GAG GCC GAG GAG GCG GCC CGC CTG GAT GTC ATG CAT GCG       192
Glu Leu Glu Glu Ala Glu Glu Ala Ala Arg Leu Asp Val Met His Ala
     50                  55                  60

GCC GAG CAG GCC CGC GTC CAG GCC CTC GAG GAG GCA GCG CGT CTC CGC       240
Ala Glu Gln Ala Arg Val Gln Ala Leu Glu Glu Ala Ala Arg Leu Arg
 65                  70                  75                  80

GCG GAG CTG GAG GCT GCC GAG GAG GCG GCG CGC CTG GAG GCC ATG CAC       288
Ala Glu Leu Glu Ala Ala Glu Glu Ala Ala Arg Leu Glu Ala Met His
                 85                  90                  95

GAG GCC GAG CAG GCC CGC TCC CAG GCC CTC GAG GAG GCA GCG CGT CTC       336
Glu Ala Glu Gln Ala Arg Ser Gln Ala Leu Glu Glu Ala Ala Arg Leu
            100                 105                 110

CGC GCG GAG CTG GAG GAA GCC GAG GAG GCG GCC CGC CTG GAT GTC ATG       384
Arg Ala Glu Leu Glu Glu Ala Glu Glu Ala Ala Arg Leu Asp Val Met
        115                 120                 125

CAT GCG GCC GAG CAG GCC CGC GTC CAG GCC CTC GAG GAG GCA GCG CGT       432
His Ala Ala Glu Gln Ala Arg Val Gln Ala Leu Glu Glu Ala Ala Arg
    130                 135                 140

CTC CGC GCG GAG CTG GAG GAG GCC GAG GAG GCG GCC CGC CTG GAG GCC       480
Leu Arg Ala Glu Leu Glu Glu Ala Glu Glu Ala Ala Arg Leu Glu Ala
145                 150                 155                 160

ATG CAC GAG GCC GAG CAG GCC CGC TCC CAG GCC CTC GAG GAG GCA GCG       528
Met His Glu Ala Glu Gln Ala Arg Ser Gln Ala Leu Glu Glu Ala Ala
                165                 170                 175

CGT CTC CGC GCG GAG CTG GAG GCG GCC GAG GAG GCG GCC CGC CTG GAT       576
Arg Leu Arg Ala Glu Leu Glu Ala Ala Glu Glu Ala Ala Arg Leu Asp
            180                 185                 190

GTC ATG CAC GAG GCC GAG CAG GCC CGT GTC CAG GCC CTC GAG GAG GCG       624
Val Met His Glu Ala Glu Gln Ala Arg Val Gln Ala Leu Glu Glu Ala
        195                 200                 205
```

-continued

```
GCG CGC CTG GAT GTC ATG CAC GAG GCC GAG CAG GCC CGC GTC CAG GCC      672
Ala Arg Leu Asp Val Met His Glu Ala Glu Gln Ala Arg Val Gln Ala
    210                 215                 220

CTC GAG GAG GCA GCG CGT CTC CGC GCG GAG CTG GAG GCG GCC GAG GAG      720
Leu Glu Glu Ala Ala Arg Leu Arg Ala Glu Leu Glu Ala Ala Glu Glu
225                 230                 235                 240

GCG GCC CGC CTG GAT GTC ATG CAC GAG GCC GAG CAG GCC CGC GTC CAG      768
Ala Ala Arg Leu Asp Val Met His Glu Ala Glu Gln Ala Arg Val Gln
                245                 250                 255

GCC CTC GAG GAG GCA GCG CGT CTC CGC GCG GAG CTG GAG GCG GCC GAG      816
Ala Leu Glu Glu Ala Ala Arg Leu Arg Ala Glu Leu Glu Ala Ala Glu
            260                 265                 270

GAG GCG GCC CGC CTG GAT GTC ATG CAC GAG GGC GAG CAG GCC CGT GTC      864
Glu Ala Ala Arg Leu Asp Val Met His Glu Gly Glu Gln Ala Arg Val
        275                 280                 285

CAG GCC CTC GAG GAG GCG GCC CGC CTG GAG GCC ATG CAC GAG GCC GAG      912
Gln Ala Leu Glu Glu Ala Ala Arg Leu Glu Ala Met His Glu Ala Glu
    290                 295                 300

CAG GCC CGC TCC CAG GCC CTC GAG GAG GCA GCG CGT CTC TGC GCG GAG      960
Gln Ala Arg Ser Gln Ala Leu Glu Glu Ala Ala Arg Leu Cys Ala Glu
305                 310                 315                 320

CTG GAG GCT GAG GAG GAG GAA AAA GAT GAG CGG CCG GCG ACG TCG AGC     1008
Leu Glu Ala Glu Glu Glu Glu Lys Asp Glu Arg Pro Ala Thr Ser Ser
                325                 330                 335

TAC AGC GAG GAG TGC AAA GGG CGA CTG CTA TCG AGG GCG CGG CCG GAT     1056
Tyr Ser Glu Glu Cys Lys Gly Arg Leu Leu Ser Arg Ala Arg Pro Asp
            340                 345                 350

CCG CGG AGG CCG CTG CCG CGG CCG TTC ATT GGG ATG TCA CTG TTG GAG     1104
Pro Arg Arg Pro Leu Pro Arg Pro Phe Ile Gly Met Ser Leu Leu Glu
        355                 360                 365

GAT GTG GAG AAG AGT ATT CTC ATT GTG GAC GGG CTC TAC AGG GAT GGG     1152
Asp Val Glu Lys Ser Ile Leu Ile Val Asp Gly Leu Tyr Arg Asp Gly
    370                 375                 380

CCG GCG TAC CAG ACG GGC ATC CGC CTC GGG GAT GTC CTC TTG CGT ATC     1200
Pro Ala Tyr Gln Thr Gly Ile Arg Leu Gly Asp Val Leu Leu Arg Ile
385                 390                 395                 400

GCG GGG GTT TAC GTG GAT TCA ATA GCG AAG GCG AGG CAG GTG GTC GAT     1248
Ala Gly Val Tyr Val Asp Ser Ile Ala Lys Ala Arg Gln Val Val Asp
                405                 410                 415

GCG CGT TGC CGC TGC GGC TGC GTC GTT CCC GTG ACG CTG GCG ACG AAG     1296
Ala Arg Cys Arg Cys Gly Cys Val Val Pro Val Thr Leu Ala Thr Lys
            420                 425                 430

ATG AAC CAG CAG TAC AGC GTG GCT CTG TAT ATC ATG ACG GTG GAT CCG     1344
Met Asn Gln Gln Tyr Ser Val Ala Leu Tyr Ile Met Thr Val Asp Pro
        435                 440                 445

CAG CAC AAC GAC AAG CCC TTT TTT TTT GAT GTG CAC ATC CAC CAC CGC     1392
Gln His Asn Asp Lys Pro Phe Phe Phe Asp Val His Ile His His Arg
    450                 455                 460

ATC GAG AGC TCG CAC ATG GGG AAG AAG GCG CAG TGG ATG GAA GTT CTT     1440
Ile Glu Ser Ser His Met Gly Lys Lys Ala Gln Trp Met Glu Val Leu
465                 470                 475                 480

GAG AGC CCA TCC GTA TCT TCG GCT GCC ACC ACC CCT CTC GTG CCG CTC     1488
Glu Ser Pro Ser Val Ser Ser Ala Ala Thr Thr Pro Leu Val Pro Leu
                485                 490                 495

TTG CGT GAG CCG ACG CCG CGT AGG GGC TCA GAG CTG CAG TCA AGT GCT     1536
Leu Arg Glu Pro Thr Pro Arg Arg Gly Ser Glu Leu Gln Ser Ser Ala
            500                 505                 510

CGT TCC GCC TTC GTT GCC ACG TCT TAC TTC TCG AGC GCG CGC AGG TCG     1584
Arg Ser Ala Phe Val Ala Thr Ser Tyr Phe Ser Ser Ala Arg Arg Ser
        515                 520                 525
```

```
GTC AGC TCA GAA AGT GAG CGA CCG CGC GGG TCC TCT AGC GTG GCT ATG      1632
Val Ser Ser Glu Ser Glu Arg Pro Arg Gly Ser Ser Ser Val Ala Met
    530                 535                 540

GCG GAG GAG GCG ATC GCG CTG GCG CCG CAA GGG TAT ACC CCA CCC AAC      1680
Ala Glu Glu Ala Ile Ala Leu Ala Pro Gln Gly Tyr Thr Pro Pro Asn
545                 550                 555                 560

CAA GTG CGC GGC CGT AGT TGACGTCTCT GTGTGAGTGT GTGTCGCTCC             1728
Gln Val Arg Gly Arg Ser
                565

GTCTCCTTCC TTTTTCGTCA TGTGTTTTAT TCATTTCTTT TTC                      1771
```

(2) INFORMATION FOR SEQ ID NO:2:

(i) SEQUENCE CHARACTERISTICS:
(A) LENGTH: 566 amino acids
(B) TYPE: amino acid
(D) TOPOLOGY: linear (ii) MOLECULE TYPE: protein (xi) SEQUENCE DESCRIPTION: SEQ ID NO:2:

```
Gln Ala Arg Val Gln Ala Leu Glu Glu Ala Ala Arg Leu Arg Ala Glu
  1               5                  10                  15

Leu Glu Ala Ala Glu Glu Ala Ala Arg Leu Asp Val Met His Ala Ala
            20                  25                  30

Glu Gln Ala Arg Val Gln Ala Leu Glu Glu Ala Ala Arg Leu Arg Ala
        35                  40                  45

Glu Leu Glu Glu Ala Glu Glu Ala Ala Arg Leu Asp Val Met His Ala
    50                  55                  60

Ala Glu Gln Ala Arg Val Gln Ala Leu Glu Glu Ala Ala Arg Leu Arg
 65                  70                  75                  80

Ala Glu Leu Glu Ala Ala Glu Glu Ala Ala Arg Leu Glu Ala Met His
                85                  90                  95

Glu Ala Glu Gln Ala Arg Ser Gln Ala Leu Glu Glu Ala Ala Arg Leu
            100                 105                 110

Arg Ala Glu Leu Glu Glu Ala Glu Glu Ala Ala Arg Leu Asp Val Met
        115                 120                 125

His Ala Ala Glu Gln Ala Arg Val Gln Ala Leu Glu Glu Ala Ala Arg
    130                 135                 140

Leu Arg Ala Glu Leu Glu Glu Ala Glu Glu Ala Ala Arg Leu Glu Ala
145                 150                 155                 160

Met His Glu Ala Glu Gln Ala Arg Ser Gln Ala Leu Glu Glu Ala Ala
                165                 170                 175

Arg Leu Arg Ala Glu Leu Glu Ala Ala Glu Glu Ala Ala Arg Leu Asp
            180                 185                 190

Val Met His Glu Ala Glu Gln Ala Arg Val Gln Ala Leu Glu Glu Ala
        195                 200                 205

Ala Arg Leu Asp Val Met His Glu Ala Glu Gln Ala Arg Val Gln Ala
    210                 215                 220

Leu Glu Glu Ala Ala Arg Leu Arg Ala Glu Leu Glu Ala Ala Glu Glu
225                 230                 235                 240

Ala Ala Arg Leu Asp Val Met His Glu Ala Glu Gln Ala Arg Val Gln
                245                 250                 255

Ala Leu Glu Glu Ala Ala Arg Leu Arg Ala Glu Leu Glu Ala Ala Glu
            260                 265                 270

Glu Ala Ala Arg Leu Asp Val Met His Glu Gly Glu Gln Ala Arg Val
        275                 280                 285
```

-continued

```
Gln Ala Leu Glu Glu Ala Ala Arg Leu Glu Ala Met His Glu Ala Glu
    290                 295                 300

Gln Ala Arg Ser Gln Ala Leu Glu Glu Ala Ala Arg Leu Cys Ala Glu
305                 310                 315                 320

Leu Glu Ala Glu Glu Glu Glu Lys Asp Glu Arg Pro Ala Thr Ser Ser
                325                 330                 335

Tyr Ser Glu Glu Cys Lys Gly Arg Leu Leu Ser Arg Ala Arg Pro Asp
            340                 345                 350

Pro Arg Arg Pro Leu Pro Arg Pro Phe Ile Gly Met Ser Leu Leu Glu
        355                 360                 365

Asp Val Glu Lys Ser Ile Leu Ile Val Asp Gly Leu Tyr Arg Asp Gly
    370                 375                 380

Pro Ala Tyr Gln Thr Gly Ile Arg Leu Gly Asp Val Leu Leu Arg Ile
385                 390                 395                 400

Ala Gly Val Tyr Val Asp Ser Ile Ala Lys Ala Arg Gln Val Val Asp
                405                 410                 415

Ala Arg Cys Arg Cys Gly Cys Val Val Pro Val Thr Leu Ala Thr Lys
            420                 425                 430

Met Asn Gln Gln Tyr Ser Val Ala Leu Tyr Ile Met Thr Val Asp Pro
        435                 440                 445

Gln His Asn Asp Lys Pro Phe Phe Phe Asp Val His Ile His His Arg
    450                 455                 460

Ile Glu Ser Ser His Met Gly Lys Lys Ala Gln Trp Met Glu Val Leu
465                 470                 475                 480

Glu Ser Pro Ser Val Ser Ser Ala Ala Thr Thr Pro Leu Val Pro Leu
                485                 490                 495

Leu Arg Glu Pro Thr Pro Arg Arg Gly Ser Glu Leu Gln Ser Ser Ala
            500                 505                 510

Arg Ser Ala Phe Val Ala Thr Ser Tyr Phe Ser Ser Ala Arg Arg Ser
        515                 520                 525

Val Ser Ser Glu Ser Glu Arg Pro Arg Gly Ser Ser Ser Val Ala Met
    530                 535                 540

Ala Glu Glu Ala Ile Ala Leu Ala Pro Gln Gly Tyr Thr Pro Pro Asn
545                 550                 555                 560

Gln Val Arg Gly Arg Ser
                565
```

(2) INFORMATION FOR SEQ ID NO:3:

(i) SEQUENCE CHARACTERISTICS:
(A) LENGTH: 33 amino acids
(B) TYPE: amino acid
(C) STRANDEDNESS:
(D) TOPOLOGY: linear (ix) FEATURE:
(A) NAME/KEY: Region
(B) LOCATION: 4
(D) OTHER INFORMATION: /note= "Xaa at Site 4 is Valine or Serine"

(ix) FEATURE:
(A) NAME/KEY: Region
(B) LOCATION: 14
(D) OTHER INFORMATION: /note= "Xaa at Site 14 is Arginine or Cysteine"

(ix) FEATURE:
(A) NAME/KEY: Region
(B) LOCATION: 19
(D) OTHER INFORMATION: /note= "Xaa at Site 19 is Alanine -continued of Glutamic Acid"

(ix) FEATURE:
(A) NAME/KEY: Region
(B) LOCATION: 20
(D) OTHER INFORMATION: /note= "Xaa at Site 20 is Alanine or Glutamic Acid"

(ix) FEATURE:
(A) NAME/KEY: Region
(B) LOCATION: 27
(D) OTHER INFORMATION: /note= "Xaa at Site 27 is Aspartic Acid or Glutamic Acid"

(ix) FEATURE:
(A) NAME/KEY: Region
(B) LOCATION: 28
(D) OTHER INFORMATION: /note= "Xaa at Site 28 is Valine or Alanine"

(ix) FEATURE:
(A) NAME/KEY: Region
(B) LOCATION: 31
(D) OTHER INFORMATION: /note= "Xaa at Site 31 is Alanine or Glutamic Acid"

(ix) FEATURE:
(A) NAME/KEY: Region
(B) LOCATION: 32
(D) OTHER INFORMATION: /note= "Xaa at Site 32 is Alanine or Glycine"

(xi) SEQUENCE DESCRIPTION: SEQ ID NO:3:

```
Gln Ala Arg Xaa Gln Ala Leu Glu Glu Ala Ala Arg Leu Xaa Ala Glu
1               5                   10                  15

Leu Glu Xaa Xaa Glu Glu Ala Ala Arg Leu Xaa Xaa Met His Xaa Xaa
            20                  25                  30

Glu
```

(2) INFORMATION FOR SEQ ID NO:4:

(i) SEQUENCE CHARACTERISTICS:
(A) LENGTH: 33 amino acids
(B) TYPE: amino acid
(C) STRANDEDNESS:
(D) TOPOLOGY: linear (xi) SEQUENCE DESCRIPTION: SEQ ID NO:4:

```
Gln Ala Arg Val Gln Ala Leu Glu Glu Ala Ala Arg Leu Arg Ala Glu
1               5                   10                  15

Leu Glu Ala Ala Glu Glu Ala Ala Arg Leu Asp Val Met His Ala Ala
            20                  25                  30

Glu
```

(2) INFORMATION FOR SEQ ID NO:5:

(i) SEQUENCE CHARACTERISTICS:
(A) LENGTH: 33 amino acids
(B) TYPE: amino acid
(C) STRANDEDNESS:
(D) TOPOLOGY: linear (xi) SEQUENCE DESCRIPTION: SEQ ID NO:5:

```
Gln Ala Arg Val Gln Ala Leu Glu Glu Ala Ala Arg Leu Arg Ala Glu
1               5                   10                  15

Leu Glu Glu Ala Glu Glu Ala Ala Arg Leu Asp Val Met His Ala Ala
            20                  25                  30

Glu
```

(2) INFORMATION FOR SEQ ID NO:6:

(i) SEQUENCE CHARACTERISTICS:
(A) LENGTH: 33 amino acids
(B) TYPE: amino acid
(C) STRANDEDNESS:
(D) TOPOLOGY: linear (xi) SEQUENCE DESCRIPTION: SEQ ID NO:6:

```
Gln Ala Arg Val Gln Ala Leu Glu Glu Ala Ala Arg Leu Arg Ala Glu
1               5                   10                  15

Leu Glu Ala Ala Glu Glu Ala Ala Arg Leu Glu Ala Met His Glu Ala
            20                  25                  30

Glu
```

(2) INFORMATION FOR SEQ ID NO:7:

(i) SEQUENCE CHARACTERISTICS:
(A) LENGTH: 33 amino acids
(B) TYPE: amino acid
(C) STRANDEDNESS:
(D) TOPOLOGY: linear (xi) SEQUENCE DESCRIPTION: SEQ ID NO:7:

```
Gln Ala Arg Ser Gln Ala Leu Glu Glu Ala Ala Arg Leu Arg Ala Glu
1               5                   10                  15

Leu Glu Glu Ala Glu Glu Ala Ala Arg Leu Asp Val Met His Ala Ala
            20                  25                  30

Glu
```

(2) INFORMATION FOR SEQ ID NO:8:

(i) SEQUENCE CHARACTERISTICS:
(A) LENGTH: 33 amino acids
(B) TYPE: amino acid
(C) STRANDEDNESS:
(D) TOPOLOGY: linear (xi) SEQUENCE DESCRIPTION: SEQ ID NO:8:

```
Gln Ala Arg Val Gln Ala Leu Glu Glu Ala Ala Arg Leu Arg Ala Glu
1               5                   10                  15

Leu Glu Glu Ala Glu Glu Ala Ala Arg Leu Glu Ala Met His Glu Ala
            20                  25                  30

Glu
```

(2) INFORMATION FOR SEQ ID NO:9:

(i) SEQUENCE CHARACTERISTICS:
(A) LENGTH: 33 amino acids
(B) TYPE: amino acid
(C) STRANDEDNESS:
(D) TOPOLOGY: linear (xi) SEQUENCE DESCRIPTION: SEQ ID NO:9:

```
Gln Ala Arg Ser Gln Ala Leu Glu Glu Ala Ala Arg Leu Arg Ala Glu
1               5                   10                  15

Leu Glu Ala Ala Glu Glu Ala Ala Arg Leu Asp Val Met His Glu Ala
            20                  25                  30

Glu
```

(2) INFORMATION FOR SEQ ID NO:10:

(i) SEQUENCE CHARACTERISTICS:

-continued

```
        (A) LENGTH: 33 amino acids
        (B) TYPE: amino acid
        (C) STRANDEDNESS:
        (D) TOPOLOGY: linear

      (xi) SEQUENCE DESCRIPTION: SEQ ID NO:10:

    Gln Ala Arg Val Gln Ala Leu Glu Glu Ala Ala Arg Leu Arg Ala Glu
    1               5                   10                  15

    Leu Glu Ala Ala Glu Glu Ala Ala Arg Leu Asp Val Met His Glu Ala
                20                  25                  30

    Glu


(2) INFORMATION FOR SEQ ID NO:11:

     (i) SEQUENCE CHARACTERISTICS:
        (A) LENGTH: 33 amino acids
        (B) TYPE: amino acid
        (C) STRANDEDNESS:
        (D) TOPOLOGY: linear

      (xi) SEQUENCE DESCRIPTION: SEQ ID NO:11:

    Gln Ala Arg Val Gln Ala Leu Glu Glu Ala Ala Arg Leu Arg Ala Glu
    1               5                   10                  15

    Leu Glu Ala Ala Glu Glu Ala Ala Arg Leu Asp Val Met His Glu Gly
                20                  25                  30

    Glu
```